(12) United States Patent
Hu et al.

(10) Patent No.: US 7,041,873 B2
(45) Date of Patent: May 9, 2006

(54) COMPOSITIONS AND METHODS FOR PROMOTING EXPRESSION OF NUCLEIC ACIDS IN PLANTS

(75) Inventors: Xu Hu, Urbandale, IA (US); Guihua Lu, Urbandale, IA (US); Richard L. Ruff, Ankeny, IA (US); Wolfgang Schuh, West Des Moines, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 471 days.

(21) Appl. No.: 10/266,416

(22) Filed: Oct. 8, 2002

(65) Prior Publication Data

US 2003/0101483 A1    May 29, 2003

Related U.S. Application Data

(60) Provisional application No. 60/329,667, filed on Oct. 16, 2001.

(51) Int. Cl.
*C12N 15/09* (2006.01)
*C12N 15/82* (2006.01)
*A01H 5/00* (2006.01)

(52) U.S. Cl. ............ 800/287; 800/278; 800/279; 800/298; 800/295; 800/317; 800/312; 435/468; 435/430.1; 536/23.4

(58) Field of Classification Search ......... 536/24.1; 800/287, 278, 312, 298, 295, 279; 435/320.1, 435/468, 430.1
See application file for complete search history.

(56) References Cited

U.S. PATENT DOCUMENTS

| | | | |
|---|---|---|---|
| 5,494,813 A * | 2/1996 | Hepher et al. | ............ 800/279 |
| 5,589,622 A | 12/1996 | Gurr et al. | |
| 5,750,386 A | 5/1998 | Conkling et al. | |
| 5,770,786 A | 6/1998 | Sijmons | |
| 5,824,876 A | 10/1998 | Gurr et al. | |
| 5,994,627 A | 11/1999 | Lagudah | |
| 6,006,470 A | 12/1999 | Geoghegan et al. | |
| 6,008,436 A | 12/1999 | Conkling et al. | |
| 6,072,050 A | 6/2000 | Bowen et al. | ............ 536/24.1 |
| 6,096,944 A | 8/2000 | Vierling et al. | |
| 6,252,138 B1 | 6/2001 | Karimi et al. | |
| 6,262,344 B1 | 7/2001 | Ohl et al. | |
| 6,284,948 B1 * | 9/2001 | Jessen et al. | ............ 800/301 |

FOREIGN PATENT DOCUMENTS

| | | |
|---|---|---|
| WO | WO 92/21757 | 12/1992 |
| WO | WO 93/10251 | 5/1993 |

OTHER PUBLICATIONS

Kim et al. Plant Molecular Biology, vol. 24, pp. 105-117, 1994.*
Keller et al. The Plant Cell, vol. 3, pp. 1051-1061, 1991.*
Urwin, et al., (1998), *Planta*, 204: 472-479, "Enhanced transgenic plant resistance to nematodes by dual proteinase inhibitor constructs".

* cited by examiner

*Primary Examiner*—Medina A. Ibrahim
(74) *Attorney, Agent, or Firm*—Pioneer Hi-Bred International, Inc.

(57) ABSTRACT

The present invention relates to nematode-regulated promoter sequences and their use in creating or enhancing nematode-resistance in plants. Nucleic acid molecules comprising a heterologous nucleotide sequence operably linked to a nematode-regulated promoter and vectors, plant cells, plants, and transformed seeds containing such constructs are provided. Methods for the creation and use of such promoters in repressing or inducing expression of a heterologous nucleotide sequence in a plant, as well as methods for creating or enhancing nematode-resistance in plants by such repression or induction of heterologous nucleotide sequences by nematode-regulated promoters are also provided.

32 Claims, 3 Drawing Sheets

CaMV 35S

SCP1

UCP3

SUP

SEQUENCE LISTING

```
<160> NUMBER OF SEQ ID NOS: 5

<210> SEQ ID NO 1
<211> LENGTH: 485
<212> TYPE: DNA
<213> ORGANISM: Artificial Sequence
<220> FEATURE:
<223> OTHER INFORMATION: Single strand and linear
<220> FEATURE:
<221> NAME/KEY: misc_feature
<222> LOCATION: (0)...(0)
<223> OTHER INFORMATION: SCP1 synthetic promoter

<400> SEQUENCE: 1
cgtcaacatg gtggagcacg acactctcgt ctactccaag aatatcaaag atacagtctc      60
agaagaccaa agggctattg agacttttca acaaagggta atatcgggaa acctcctcgg     120
attccattgc ccagctatct gtcacttcat caaaaggaca gtagaaaagg aaggtggcac     180
ctacaaatgc catcattgcg ataaaggaaa ggctatcgtt caagatgcct ctgccgacag     240
tggtcccaaa gatggacccc cacccacgag gagcatcgtg gaaaagaag acgttccaac      300 cacgtcttca aagcaagtgg attgatgtga tgatcctatg cgtatggtat gacgtgtgtt     360
caagatgatg acttcaaacc tacctatgac gtatggtatg acgtgtgtcg actgatgact     420
tagatccact cgagcggcta taaatacgta cctacgcacc ctgcgctacc atccctagag     480
ctgca                                                                  485

<210> SEQ ID NO 2
<211> LENGTH: 2609
<212> TYPE: DNA
<213> ORGANISM: Artificial Sequence
<220> FEATURE:
<223> OTHER INFORMATION: Single strand and linear
<220> FEATURE:
<221> NAME/KEY: misc_feature
<222> LOCATION: (0)...(0)
<223> OTHER INFORMATION: UCP3 synthetic promoter

<400> SEQUENCE: 2
tctagagata atgagcattg catgtctaag ttataaaaaa ttaccacata tttttttgt       60 cacacttgtt tgaagtgcag tttatctatc tttatacata tatttaaact ttactctacg     120
aataatataa tctatagtac tacaataata tcagtgtttt agagaatcat ataaatgaac     180
agttagacat ggtctaaagg acaattgagt attttgacaa caggactcta cagtttate     240 tttttagtgt gcatgtgttc tccttttttt ttgcaaatag cttcacctat ataatacttc    300
```

-continued

```
atccatttta ttagtacatc catttagggt ttagggttaa tggtttttat agactaattt      360
ttttagtaca tctattttat tctattttag cctctaaatt aagaaaacta aaactctatt      420 ttagttttt tatttaataa tttagatata aaatagaata aaataaagtg actaaaaatt       480
aaacaaatac cctttaagaa attaaaaaaa ctaaggaaac attttcttg tttcgagtag       540 ataatgccag cctgttaaac gccgtcgacg agtctaacgg acaccaacca gcgaaccagc      600
agcgtcgcgt cgggccaagc gaagcagacg gcacggcatc tctgtcgctg cctctggacc     660
cctctcgaga gttccgctcc accgttggac ttgctccgct gtcggcatcc agaaattgcg      720
tggcggagcg gcagacgtga gccggcacgg caggcggcct cctcctcctc tcacggcacc      780
ggcagctacg ggggattcct ttcccaccgc tcctactaga gataatgagc attgcatgtc     840
taagttataa aaaattacca catatttttt ttgtcacact tgtttgaagt gcagtttatc      900
tatctttata catatattta aactttactc tacgaataat ataatctata gtactacaat     960
aatatcagtg ttttagagaa tcatataaat gaacagttag acatggtcta aaggacaatt    1020
gagtattttg acaacaggac tctacagttt tatcttttta gtgtgcatgt gttctccttt    1080 tttttttgcaa atagcttcac ctatataata cttcatccat tttattagta catccatta     1140 gggtttaggg ttaatggttt ttatagacta atttttttag tacatctatt ttattctatt    1200
ttagcctcta aattaagaaa actaaaactc tattttagtt tttttattta ataatttaga    1260
tataaaatag aataaaataa agtgactaaa aattaaacaa ataccctta agaaattaaa      1320 aaaactaagg aaacatttt cttgtttcga gtagataatg ccagcctgtt aaacgccgtc     1380
gacgagtcta acggacacca accagcgaac cagcagcgtc gcgtcgggcc aagcgaagca    1440
gacggcacgg catctctgtc gctgcctctg gaccctctc gagagttccg ctccaccgtt     1500
ggacttgctc cgctgtcggc atccagaaat tgcgtggcgg agcggcagac gtgagccggc    1560
acggcaggcg gcctcctcct cctctcacgg caccggcagc tacgggggat ccttttccca   1620
ccgctcctac tagagataat gagcattgca tgtctaagtt ataaaaaatt accacatatt    1680 tttttttgtca cacttgtttg aagtgcagtt tatctatctt tatacatata tttaaacttt   1740
actctacgaa taatataatc tatagtacta caataatatc agtgttttag agaatcatat    1800
aaatgaacag ttagacatgg tctaaaggac aattgagtat tttgacaaca ggactctaca    1860
gttttatctt tttagtgtgc atgtgttctc cttttttttt gcaaatagct tcacctatat    1920
aatacttcat ccattttatt agtacatcca tttagggttt agggttaatg gtttttatag    1980
actaattttt ttagtacatc tatttatc tattttagcc tctaaattaa gaaaactaaa     2040
actctatttt agttttttta tttaataatt tagatataaa atagaataaa ataaagtgac    2100
taaaaattaa acaaataccc tttaagaaat taaaaaaact aaggaaacat ttttcttgtt    2160
tcgagtagat aatgccagcc tgttaaacgc cgtcgacgag tctaacggac accaaccagc    2220
gaaccagcag cgtcgcgtcg ggccaagcga agcagacggc acggcatctc tgtcgctgcc    2280
tctggacccc tctcgagagt tccgctccac cgttggactt gctccgctgt cggcatccag    2340
aaattgcgtg gcggagcggc agacgtgagc cggcacggca ggcggcctcc tcctcctctc    2400
acggcaccgg cagctacggg ggattccttt cccaccgctc ctactagaac tagtggatcc    2460
tatgcgtatg gtatgacgtg tgttcaagat gatgacttca aacctaccta tgacgtatgg    2520
tatgacgtgt gtcgactgat gacttagatc cactcgagcg gctataaata cgtacctacg    2580
caccctgcgc taccatccct agagctgca                                       2609
```

<210> SEQ ID NO 3
<211> LENGTH: 1413
<212> TYPE: DNA
<213> ORGANISM: Artificial Sequence
<220> FEATURE:
<223> OTHER INFORMATION: Single strand and linear
<220> FEATURE:
<221> NAME/KEY: misc_feature
<222> LOCATION: (0)...(0)
<223> OTHER INFORMATION: SUP synthetic promoter

<400> SEQUENCE: 3

| | | | | | |
|---|---|---|---|---|---|
| cgtcaacatg | gtggagcacg | acactctcgt | ctactccaag | aatatcaaag | atacagtctc | 60 |
| agaagaccaa | agggctattg | agacttttca | acaaagggta | atatcgggaa | acctcctcgg | 120 |
| attccattgc | ccagctatct | gtcacttcat | caaaaggaca | gtagaaaagg | aaggtggcac | 180 |
| ctacaaatgc | catcattgcg | ataaaggaaa | ggctatcgtt | caagatgcct | ctgccgacag | 240 |
| tggtcccaaa | gatggacccc | cacccacgag | gagcatcgtg | gaaaagaag | acgttccaac | 300 |
| cacgtcttca | aagcaagtgg | attgatgtga | tgatcctatg | cgtatggtat | gacgtgtgtt | 360 |
| caagatgatg | acttcaaacc | tacctatgac | gtatggtatg | acgtgtgtcg | actgatgact | 420 |
| tagatccact | cgactagaga | taatgagcat | tgcatgtcta | agttataaaa | aattaccaca | 480 |
| tatttttttt | gtcacacttg | tttgaagtgc | agtttatcta | tctttataca | tatatttaaa | 540 |
| ctttactcta | cgaataatat | aatctatagt | actacaataa | tatcagtgtt | ttagagaatc | 600 |
| atataaatga | acagttagac | atggtctaaa | ggacaattga | gtattttgac | aacaggactc | 660 |
| tacagtttta | tcttttagt | gtgcatgtgt | tctccttttt | ttttgcaaat | agcttcacct | 720 |
| atataatact | tcatccattt | tattagtaca | tccatttagg | gtttagggtt | aatggttttt | 780 |
| atagactaat | ttttttagta | catctatttt | attctatttt | agcctctaaa | ttaagaaaac | 840 |
| taaaactcta | ttttagtttt | tttatttaat | aatttagata | taaaatagaa | taaaataaag | 900 |
| tgactaaaaa | ttaaacaaat | accctttaag | aaattaaaaa | aactaaggaa | acattttcc | 960 |
| tgtttcgagt | agataatgcc | agcctgttaa | acgccgtcga | cgagtctaac | ggacaccaac | 1020 |
| cagcgaacca | gcagcgtcgc | gtcgggccaa | gcgaagcaga | cggcacggca | tctctgtcgc | 1080 |
| tgcctctgga | cccctctcga | gagttccgct | ccaccgttgg | acttgctccg | ctgtcggcat | 1140 |
| ccagaaattg | cgtggcggag | cggcagacgt | gagccggcac | ggcaggcggc | ctcctcctcc | 1200 |
| tctcacggca | ccggcagcta | cggggggattc | ctttcccacc | gctcctacta | gaactagtgg | 1260 |
| atcctatgcg | tatggtatga | cgtgtgttca | agatgatgac | ttcaaaccta | cctatgacgt | 1320 |
| atggtatgac | gtgtgtcgac | tgatgactta | gatccactcg | agcggctata | aatacgtacc | 1380 |
| tacgcaccct | gcgctaccat | ccctagagct | gca | | | 1413 |

<210> SEQ ID NO 4
<211> LENGTH: 332
<212> TYPE: DNA
<213> ORGANISM: Caulimovirus
<220> FEATURE:
<221> NAME/KEY: misc_feature
<222> LOCATION: (0)...(0)
<223> OTHER INFORMATION: Upstream activating region of 35S CaMV promoter

<400> SEQUENCE: 4

| | | | | | |
|---|---|---|---|---|---|
| cgtcaacatg | gtggagcacg | acactctcgt | ctactccaag | aatatcaaag | atacagtctc | 60 |
| agaagaccaa | agggctattg | agacttttca | acaaagggta | atatcgggaa | acctcctcgg | 120 |
| attccattgc | ccagctatct | gtcacttcat | caaaaggaca | gtagaaaagg | aaggtggcac | 180 |

```
ctacaaatgc catcattgcg ataaaggaaa ggctatcgtt caagatgcct ctgccgacag    240
tggtcccaaa gatggacccc cacccacgag gagcatcgtg gaaaagaag acgttccaac    300 cacgtcttca aagcaagtgg attgatgtga tg                                  332

<210> SEQ ID NO 5
<211> LENGTH: 813
<212> TYPE: DNA
<213> ORGANISM: Zea mays
<220> FEATURE:
<221> NAME/KEY: misc_feature
<222> LOCATION: (0)...(0)
<223> OTHER INFORMATION: Upstream activating region of maize ubiquitin-1
      promoter

<400> SEQUENCE: 5
tctagagata atgagcattg catgtctaag ttataaaaaa ttaccacata tttttttgt     60 cacacttgtt tgaagtgcag tttatctatc tttatacata tatttaaact ttactctacg   120
aataatataa tctatagtac tacaataata tcagtgtttt agagaatcat ataaatgaac   180
agttagacat ggtctaaagg acaattgagt attttgacaa caggactcta cagttttatc   240
tttttagtgt gcatgtgttc tccttttttt ttgcaaatag cttcacctat ataatacttc   300
atccatttta ttagtacatc catttagggt ttagggttaa tggtttttat agactaattt   360
ttttagtaca tctatttat tctatttag cctctaaatt aagaaaacta aaactctatt    420
ttagtttttt tatttaataa tttagatata aaatagaata aaataaagtg actaaaaatt   480
aaacaaatac cctttaagaa attaaaaaaa ctaaggaaac attttcttg tttcgagtag    540 ataatgccag cctgttaaac gccgtcgacg agtctaacgg acaccaacca gcgaaccagc   600
agcgtcgcgt cgggccaagc gaagcagacg gcacggcatc tctgtcgctg cctctggacc   660
cctctcgaga gttccgctcc accgttggac ttgctccgct gtcggcatcc agaaattgcg   720
tggcggagcg gcagacgtga gccggcacgg caggcggcct cctcctcctc tcacggcacg   780
gcagctacgg gggattcctt tcccaccgct cct                                813
```

US 7,041,873 B2

COMPOSITIONS AND METHODS FOR PROMOTING EXPRESSION OF NUCLEIC ACIDS IN PLANTS

CROSS REFERENCE TO RELATED APPLICATION

This application claims the benefit of U.S. Provisional Application No. 60/329,667 filed Oct. 16, 2001 and hereby incorporated by reference.

FIELD OF THE INVENTION

The present invention relates to compositions comprising nematode-regulated promoter sequences and their use in creating or enhancing nematode-resistance in plants.

BACKGROUND OF THE INVENTION

Nematodes are small, worm-like animals frequently associated with a variety of destructive diseases in plants, animals, and humans. Pathogenic nematodes are a major agricultural problem, causing significant crop and yield losses worldwide. The potato cyst nematodes *Globodera rostochiensis* and *Globodera pallida,* for example, are key pests of the potato, while the beet cyst nematode *Heterodera schachtii* is a major problem for sugar beet growers in Europe and the United States. Furthermore, losses due to these nematodes have enormous economic impact. For example, losses due to the soybean cyst nematode (SCN) *Heterodera glycines* may exceed $500 million/year in the United States alone, or about 10% of the total $5.8 billion/year of agricultural losses due to nematode destruction of crops in the United States.

Because of the large costs of nematode-related agricultural losses, a variety of methods for controlling nematodes in plants have been developed, primarily involving the use of highly toxic chemical nematicides. Thus, although naturally nematode-resistant varieties of crop plants can be used to reduce the effects of nematodes on crops, in general, control has focused on the use of highly potent carbamate chemicals such as Aldicarb™ (Rhone-Poulenc Ag. Co). In 1982, in the United States alone over 100 million pounds of such nematicides were applied to crops. However, the use of chemical nematicides has been restricted in recent years because such compounds have been shown to be highly toxic to mammals. Thus, there is a real need for effective non-chemical nematicides and methods for the treatment of nematode diseases in plants.

One such method is the production of transgenic plants that are resistant to nematode infections. For example, with the use of nematode-inducible promoters, plants can be genetically altered to express nematicidal proteins in response to exposure to nematodes. See, for example, U.S. Pat. No. 6,252,138, herein incorporated by reference. Alternatively, some methods use a combination of both nematode-inducible and nematode-repressible promoters to obtain nematode resistance. Thus, WO 92/21757, herein incorporated by reference, discusses the use of a two-promoter system for disrupting nematode feeding sites, where one nematode-inducible promoter drives expression of a toxic product that kills the plant cells at the feeding site, while the other nematode-repressible promoter drives expression of a gene product that inactivates the toxic product of the first promoter under circumstances in which nematodes are not present, thereby allowing for tighter control of the deleterious effects of the toxic product on plant tissue.

Although these methods have potential for the treatment of nematode infections, their effectiveness is heavily dependent upon the characteristics of the nematode-inducible or nematode-repressible promoters discussed above. Thus, such factors as the strength of such nematode-responsive promoters, degree of induction or repression, tissue specificity, or the like can all alter the effectiveness of these disease resistance methods. Consequently, there is a continued need for the identification of nematode-regulated promoters for use in promoting nematode resistance.

SUMMARY OF THE INVENTION

Compositions and methods for promoting nematode resistance in plants are provided. Compositions include nucleic acid molecules comprising a heterologous nucleotide or nematode-resistance sequence operably linked to nematode-regulated promoters, specifically the synthetic nematode-regulated promoters designated herein as SCP1, UCP3, or SUP, as well as vectors and transformed plant cells, plants, and seeds comprising these constructs.

In particular, a nucleic acid molecule comprising a heterologous nematode-resistance sequence operably linked to a promoter capable of driving transcription of said heterologous nematode-resistance sequence in a plant cell, wherein said promoter comprises a nucleotide sequence selected from the group consisting of:

(a) a nucleotide sequence comprising the sequence set forth in SEQ ID NO:1, SEQ ID NO:2 or SEQ ID NO:3;

(b) a nucleotide sequence comprising at least 20 contiguous nucleotides of the sequence of SEQ ID NO:1, SEQ ID NO:2 or SEQ ID NO:3, wherein said nucleotide sequence has nematode-inducible promoter activity; and (c) a nucleotide sequence having at least 70% sequence identity to the sequence of SEQ ID NO:1, SEQ ID NO:2 or SEQ ID NO:3, wherein said nucleotide sequence has nematode-inducible promoter activity is disclosed.

In a further embodiment, a nucleic acid molecule comprising a heterologous nucleotide sequence operably linked to a promoter capable of regulating expression of said heterologous nucleotide sequence in a plant cell in response to a nematode stimulus, wherein said promoter comprises a nucleotide sequence selected from the group consisting of:

(a) a nucleotide sequence comprising the sequence set forth in SEQ ID NO:1, SEQ ID NO:2, or SEQ ID NO:3;

(b) a nucleotide sequence comprising at least 20 contiguous nucleotides of the sequence of SEQ ID NO:1, SEQ ID NO:2, or SEQ ID NO:3, wherein said nucleotide sequence has nematode-regulated promoter activity; and (c) a nucleotide sequence having at least 70% sequence identity to the sequence of SEQ ID NO:1, SEQ ID NO:2, or SEQ ID NO:3, wherein said nucleotide sequence has nematode-regulated promoter activity is disclosed.

In addition, a nucleic acid molecule comprising a first nucleotide sequence comprising a heterologous nematode-resistance sequence operably linked to a first promoter capable of inducing transcription of said heterologous nematode-resistance sequence in a plant cell and a second nucleotide sequence comprising a sequence capable of inhibiting said heterologous nematode-resistance sequence operably linked to a second promoter capable of repressing transcription of said inhibitor of said heterologous nematode-resistance sequence in a plant cell, wherein said first promoter comprises a nucleotide sequence selected from the group consisting of:

(a) a nucleotide sequence comprising the sequence set forth in SEQ ID NO:2, or SEQ ID NO:3;

(b) a nucleotide sequence comprising at least 20 contiguous nucleotides of the sequence of SEQ ID NO:2, or SEQ ID NO:3, wherein said nucleotide sequence has nematode-regulated promoter activity; and (c) a nucleotide sequence having at least 70% sequence identity to the sequence of SEQ ID NO:2, or SEQ ID NO:3, wherein said nucleotide sequence has nematode-regulated promoter activity; and said second promoter comprises a nucleotide sequence selected from the group consisting of:

(a) a nucleotide sequence comprising the sequence set forth in SEQ ID NO:1;

(b) a nucleotide sequence comprising at least 20 contiguous nucleotides of the sequence of SEQ ID NO:1, wherein said nucleotide sequence has nematode-repressible promoter activity; and (c) a nucleotide sequence having at least 70% sequence identity to the sequence of SEQ ID NO:1, wherein said nucleotide sequence has nematode-repressible promoter activity is disclosed.

In yet a further embodiment, a nucleic acid molecule comprising a heterologous nucleotide sequence operably linked to a modified promoter capable of regulating the expression of said heterologous nucleotide sequence in response to a nematode stimulus, wherein said modified promoter comprises a promoter sequence operably linked to at least one copy of at least one sequence selected from the group consisting of:

(a) a nucleotide sequence comprising the sequence set forth in SEQ ID NO:4 or SEQ ID NO:5;

(b) a nucleotide sequence comprising a fragment of the sequence of SEQ ID NO:4 or SEQ ID NO:5, wherein said fragment comprises at least one nematode-responsive cis-acting element; and (c) a nucleotide sequence having at least 70% sequence identity to the sequence of SEQ ID NO:4 or SEQ ID NO:5 and which comprises at least one nematode-responsive cis-acting element is disclosed.

Also provided are methods for the use of such nucleic acid molecules in repressing or inducing expression of a heterologous nucleotide or nematode-resistance sequence in a plant. The methods find use in creating or enhancing nematode resistance in plants.

Specifically, a method for inducing expression of a heterologous nematode-resistance sequence in a plant, said method comprising transforming a plant cell with a nucleic acid molecule comprising said heterologous nematode-resistance sequence operably linked to a promoter capable of driving transcription of said heterologous nematode-resistance sequence in a plant cell in response to a nematode stimulus, regenerating a stably transformed plant from said plant cell, and exposing said plant to said nematode stimulus, wherein said promoter comprises a nucleotide sequence selected from the group consisting of:

(a) a nucleotide sequence comprising the sequence set forth in SEQ ID NO:1, SEQ ID NO:2 or SEQ ID NO:3;

(b) a nucleotide sequence comprising at least 20 contiguous nucleotides of the sequence of SEQ ID NO:1, SEQ ID NO:2 or SEQ ID NO:3, wherein said nucleotide sequence has nematode-inducible promoter activity; and (c) a nucleotide sequence having at least 70% sequence identity to the sequence of SEQ ID NO:1, SEQ ID NO:2 or SEQ ID NO:3 wherein said nucleotide sequence has nematode-inducible promoter activity is disclosed.

In a further embodiment, a method for expressing a nucleic acid molecule a plant, said method comprising transforming a plant cell with a nucleic acid molecule comprising a first nucleotide sequence comprising a heterologous nematode-resistance sequence operably linked to a first promoter capable of inducing transcription of said heterologous nematode-resistance sequence in a plant cell and a second nucleotide sequence comprising a sequence capable of inhibiting said heterologous nematode-resistance sequence operably linked to a second promoter capable of repressing transcription of said inhibitor of said heterologous nematode-resistance sequence in a plant cell in response to a nematode stimulus, regenerating a stably transformed plant from said plant cell, and exposing said plant to said nematode stimulus, wherein said first promoter comprises a nucleotide sequence selected from the group consisting of:

(a) a nucleotide sequence comprising the sequence set forth in SEQ ID NO:2, or SEQ ID NO:3;

(b) a nucleotide sequence comprising at least 20 contiguous nucleotides of the sequence of SEQ ID NO:2, or SEQ ID NO:3, wherein said nucleotide sequence has nematode-regulated promoter activity; and (c) a nucleotide sequence having at least 70% sequence identity to the sequence of SEQ ID NO:2, or SEQ ID NO:3, wherein said nucleotide sequence has nematode-regulated promoter activity; and said second promoter comprises a nucleotide sequence selected from the group consisting of:

(a) a nucleotide sequence comprising the sequence set forth in SEQ ID NO:1;

(b) a nucleotide sequence comprising at least 20 contiguous nucleotides of the sequence of SEQ ID NO:1, wherein said nucleotide sequence has nematode-repressible promoter activity; and (c) a nucleotide sequence having at least 70% sequence identity to the sequence of SEQ ID NO:1, wherein said nucleotide sequence has nematode-repressible promoter activity is disclosed.

In addition, a method for altering expression of a heterologous nucleotide sequence in a plant, said method comprising transforming a plant cell with a nucleic acid molecule comprising said heterologous nucleotide sequence operably linked to a promoter capable of regulating expression of said heterologous nucleotide sequence in a plant cell in response to a nematode stimulus, regenerating a stably transformed plant from said plant cell, and exposing said plant to said nematode stimulus, wherein said promoter comprises a nucleotide sequence selected from the group consisting of:

(a) a nucleotide sequence comprising the sequence set forth in SEQ ID NO:1, SEQ ID NO:2, or SEQ ID NO:3;

(b) a nucleotide sequence comprising at least 20 contiguous nucleotides of the sequence of SEQ ID NO:1, SEQ ID NO:2, or SEQ ID NO:3, wherein said nucleotide sequence has nematode-regulated promoter activity; and (c) a nucleotide sequence having at least 70% sequence identity to the sequence of SEQ ID NO:1, SEQ ID NO:2, or SEQ ID NO:3, wherein said nucleotide sequence has nematode-regulated promoter activity is disclosed.

In yet a further embodiment, a method for altering expression of a heterologous nucleotide sequence in a plant, said method comprising transforming a plant cell with a nucleic acid molecule comprising said heterologous nucleotide sequence operably linked to a modified promoter capable of regulating expression of said heterologous nucleotide sequence in a plant cell in response to a nematode stimulus, regenerating a stably transformed plant from said plant cell, and exposing said plant to said nematode stimulus, wherein said modified promoter comprises a promoter sequence operably linked to at least one copy of at least one sequence selected from the group consisting of:

(a) a nucleotide sequence comprising the sequence set forth in SEQ ID NO:4 or SEQ ID NO:5;

(b) a nucleotide sequence comprising a fragment of the sequence of SEQ ID NO:4 or SEQ ID NO:5, wherein said fragment comprises at least one nematode-responsive cis-acting element; and (c) a nucleotide sequence having at least 70% sequence identity to the sequence of SEQ ID NO:4 or SEQ ID NO:5 and which comprises at least one nematode-responsive cis-acting element is disclosed.

Further, a method for regulating nematode resistance in a plant, said method comprising transforming a plant cell with a nucleic acid molecule comprising a first nucleotide sequence comprising a heterologous nematode-resistance sequence operably linked to a first promoter capable of inducing transcription of said heterologous nematode-resistance sequence in a plant cell and a second nucleotide sequence comprising a sequence capable of inhibiting said heterologous nematode-resistance sequence operably linked to a second promoter capable of repressing transcription of said inhibitor of said heterologous nematode-resistance sequence in a plant cell in response to a nematode stimulus and regenerating stably transformed plants, wherein said first promoter comprises a nucleotide sequence selected from the group consisting of:

(a) a nucleotide sequence comprising the sequence set forth in SEQ ID NO:2, or SEQ ID NO:3;

(b) a nucleotide sequence comprising at least 20 contiguous nucleotides of the sequence of SEQ ID NO:2, or SEQ ID NO:3, wherein said nucleotide sequence has nematode-regulated promoter activity; and (c) a nucleotide sequence having at least 70% sequence identity to the sequence of SEQ ID NO:2, or SEQ ID NO:3, wherein said nucleotide sequence has nematode-regulated promoter activity; and said second promoter comprises a nucleotide sequence selected from the group consisting of:

(a) a nucleotide sequence comprising the sequence set forth in SEQ ID NO:1;

(b) a nucleotide sequence comprising at least 20 contiguous nucleotides of the sequence of SEQ ID NO:1, wherein said nucleotide sequence has nematode-repressible promoter activity; and (c) a nucleotide sequence having at least 70% sequence identity to the sequence of SEQ ID NO:1, wherein said nucleotide sequence has nematode-repressible promoter activity is disclosed.

Additionally, a method of creating or enhancing disease resistance in a plant, said method comprising transforming said plant with a nucleic acid molecule comprising a heterologous nematode-resistance sequence operably linked to a promoter that is capable of driving transcription of said nematode-resistance sequence in a plant cell in response to a nematode stimulus and regenerating stably transformed plants, wherein said promoter comprises a nucleotide sequence selected from the group consisting of:

(a) a nucleotide sequence comprising the sequence set forth in SEQ ID NO:1, SEQ ID NO:2 or SEQ ID NO:3;

(b) a nucleotide sequence comprising at least 20 contiguous nucleotides of the sequence of SEQ ID NO:1, SEQ ID NO:2 or SEQ ID NO:3, wherein said nucleotide sequence has nematode-inducible promoter activity; and (c) a nucleotide sequence having at least 70% sequence identity to the sequence of SEQ ID NO:1, SEQ ID NO:2 OR SEQ ID NO:3, wherein said nucleotide sequence has nematode-inducible promoter activity is disclosed.

A method for modifying any given promoter to obtain a nematode-regulated promoter is also provided. The method comprises the modification of the promoter to comprise at least one copy of at least one upstream activating region (UAR) identified herein as containing at least one nematode-responsive cis-acting element. The resulting promoters find use in regulating expression of heterologous sequences of interest in nematode-infected plants.

Specifically, a method for preparing a nematode-regulated promoter, said method comprising obtaining a promoter that drives expression of an operably linked heterologous nucleotide sequence and modifying said promoter to further comprise at least one copy of at least one nucleotide sequence selected from the group consisting of:

(a) a nucleotide sequence comprising the sequence set forth in SEQ ID NO:4 or SEQ ID NO:5;

(b) a nucleotide sequence comprising a fragment of the sequence of SEQ ID NO:4 or SEQ ID NO:5, wherein said fragment comprises at least one nematode-responsive cis-acting element; and (c) a nucleotide sequence having at least 70% sequence identity to the sequence of SEQ ID NO:4 or SEQ ID NO:5 and which comprises at least one nematode-responsive cis-acting element is disclosed.

DETAILED DESCRIPTION OF THE INVENTION

Figure 1:
FIG. 1 shows a schematic representation of the SCP1, UCP3, SUP, and CaMV 35S promoters. 35SUAR is the upstream region (−90 to −421) of the CaMV 35S promoter; Rsyn7-SynII is a synthetic core promoter, and UbiUAR is the upstream sequence region (−55 to −867) of the maize ubiquitin-1 promoter.
Figure 1:
Figure 1:
Figure 1:

The present invention relates to compositions and methods for promoting pathogen resistance in plants, more particularly nematode resistance. The compositions of the invention are nucleic acid molecules comprising a heterologous nucleotide sequence operably linked to a nematode-regulated promoter sequence, more particularly the synthetic promoter sequence designated SCP1 (SEQ ID NO:1), the synthetic promoter sequence designated UCP3 (SEQ ID NO:2), the synthetic promoter sequence designated SUP (SEQ ID NO:3), or a variant or a fragment thereof having nematode-regulated promoter activity. SCP1 and UCP3 are synthetic promoters previously described in U.S. Pat. No. 6,072,050. SCP1 is a synthetic hybrid promoter consisting of the upstream activating region (UAR) of the 35S CaMV promoter from Cauliflower Mosaic Virus (CaMV) operably linked to the Rsyn7-Syn II core promoter. UCP3 is a synthetic hybrid promoter consisting of three copies (in forward orientation) of the UAR (−876 to −55) of the ubiquitin-1 promoter from *Zea mays* operably linked to the Rsyn7-Syn II core promoter. These synthetic promoters are known to have constitutive promoter activity in a variety of dicot plant tissues, including stem, leaf, root, and floral tissues. See U.S. Pat. No. 6,072,050, herein incorporated by reference. SUP is a synthetic hybrid promoter consisting of one copy of the UAR of the 35S CaMV promoter from CaMV operably linked to the Rsyn7 element, which is operably linked to one copy of the UAR region of the ubiquitin-1 promoter from *Zea mays*, which is operably linked to the Rsyn7-SynII core promoter. SCP1, UCP3, and SUP are identified herein as having nematode-regulated promoter activity, and thus are referred to as nematode-regulated promoters. In addition to these promoter sequences, the nematode-regulated promoters in the compositions of the invention encompass fragments and variants of these promoters, with the definitions of such fragments and variants provided elsewhere herein.

By "nematode-regulated promoter" a promoter whose transcription initiation activity is either induced or repressed in response to a nematode stimulus is intended. Thus, a nematode-inducible promoter increases expression of an operably linked nucleotide sequence in the presence of a nematode stimulus. In contrast, a nematode-repressible promoter decreases the transcription of an operably linked nucleotide sequence in the presence of a nematode stimulus. As noted in the Examples below, SCP1 exhibits strong promoter activity in various root tissues, including, for example, cortex, pericycle, and vascular cylinder tissues of uninfected roots and in early-stage nematode-infected roots. This synthetic promoter exhibits decreased promoter activity with progression of nematode infection, and hence exhibits nematode-repressible promoter activity. In contrast, UCP3 exhibits a much lower level of promoter activity in uninfected roots, with significantly induced promoter activity following nematode infection. The SUP synthetic promoter exhibits on average stronger promoter activity in uninfected transgenic hairy roots in comparison to UCP3. Following infection with SCN, histochemical analysis of SUP promoter activity indicates higher than baseline levels near feeding sites. The SUP and UCP3 synthetic promoters are thus referred to herein as nematode-inducible promoters.

When using a nematode-inducible or nematode-repressible promoter, expression of the operably linked nucleotide sequence is initiated or inhibited, respectively, in cells in response to a nematode stimulus. As used herein, "nematode stimulus" refers to a nematode-derived agent capable of acting as a stimulus to initiate or repress nematode-regulated promoter activity as described herein. "Nematode stimulus" is contemplated to include nematodes and fragments thereof, such as proteins, nucleic acids, cell wall components, and the like as would be known to the skilled artisan to act as a stimulus for a nematode-inducible or nematode-repressible promoter. Nematode stimulus also includes a signal resulting from nematode infection, wounding, and the like. For example, proteins, nucleic acids, secondary metabolites, peptides, chemicals, and the like released during nematode parasitism or as a result of nematode wounding fall within the definition of nematode stimulus contemplated herein.

"Nematodes," as defined herein, refers to parasitic nematodes such as cyst, root-knot, and lesion nematodes, including *Heterodera* spp, *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); *Globodera rostochiensis* and *Globodera pailida* (potato cyst nematodes). Other examples of nematodes contemplated in the present invention are given elsewhere herein.

Thus, the nematode-inducible and nematode-repressible synthetic promoter sequences disclosed herein, when assembled within a nucleic acid molecule such that the promoter is operably linked to a heterologous nucleotide sequence of interest, enable expression or repression (inhibition) of expression of the heterologous nucleotide sequence in the cells of a plant stably transformed with this nucleic acid molecule. By "heterologous nucleotide sequence" a sequence that is not naturally occurring with the promoter sequence is intended. While this nucleotide sequence is heterologous to the promoter sequence, it may be homologous, or native, or heterologous, or foreign, to the plant host. By "operably linked" a functional linkage between a promoter and a second sequence, wherein the promoter sequence initiates and mediates transcription of the DNA sequence corresponding to the second sequence is intended. Generally, operably linked means that the nucleic acid sequences being linked are contiguous and, where necessary to join two protein coding regions, contiguous and in the same reading frame.

The type of heterologous nucleotide sequence within a nucleic acid molecule of the invention depends upon its intended use. Thus, when the nucleic acid molecule comprises a nematode-inducible promoter, more particularly the UCP3 or SUP promoter (SEQ ID NO:2 and SEQ ID NO:3, respectively), the heterologous nucleotide sequence of interest is a pathogen-resistance sequence, more particularly a nematode-resistance sequence. By "nematode-resistance sequence" a sequence coding for an RNA and/or a protein or polypeptide that, when expressed, either inhibits, prevents, or repels nematode infection or invasion of a plant cell, thereby limiting the spread and reproduction of the nematode is intended. Such sequences include sequences encoding nematode-resistance proteins and cytotoxic proteins or polypeptides that disrupt cell metabolism, the byproducts of which are essential for nematode survival and/or reproduction. Expression of such sequences allows a plant to avoid the disease symptoms associated with nematode infections, or prevent or minimize nematodes from causing disease and associated disease symptoms. These sequences may function as nematicides, that is as nematode-killing sequences. Such killing may occur by direct action on nematodes, or by action on the cells of the plant on which the nematodes feed to kill those cells, thereby depriving the infecting nematodes of a site of entry and/or of feeding. Alternatively, such nematicides may act on other surrounding tissue to cause the release of nematode toxins from that tissue. Such nematode-resistance sequences are provided in, for example, U.S. Pat. Nos. 5,750,386; 5,994,627; 6,006,470; and 6,228,992, incorporated herein by reference. Other examples of nematode resistance genes include Oryzacystatin-1 and cowpea trypsin inhibitor (Urwin et al. (1998) *Planta* 204: 472–479); Rhg (Webb et al (1995) *Theor. Appl. Genet.* 91: 574–581); Hs1 (Cai et al. (1997) *Science* 275: 832–834); CRE3 (Lagudah et al. (1997) *Genome* 40: 650–665); all of which are herein incorporated by reference.

Examples of nematode-resistance sequences that code for cytotoxic substances include, but are not limited to, enzymes capable of degrading nucleic acids (DNA, RNA) such as nucleases, restriction endonucleases (such as EcoRI), micrococcal nucleases, Rnase A, and barnase (i.e., mature *Bacillus amyloliquefaciens* Rnase; Mariani et al. (1990) *Nature* 347: 737–741) and Paddon and Hartley (1985) *Gene* 40:231–39); enzymes that attack proteins such as proteases, trypsin, pronase A, carboxypeptidase, endoproteinase Asp-N, endoproteinase Glu-C, and endoproteinase Lys-C; ribonucleases such as RNase CL-3 and RNase $T_1$; toxins from plant pathogenic bacteria such as phaseolotoxin, tabtoxin, and syringotoxin; lipases such as those produced from porcine pancrease and *Candida cyclindracea;* membrane channel proteins such as glp F and connexins; gap junction proteins; and antibodies that bind proteins in the cell so that the cell is thereby killed or debilitated. Genes that produce antibodies to plant cell proteins can be produced as described in Huse et al (1989) *Science* 246:1275–1281. Proteins to which such antibodies can be directed include, but are not limited to, RNA polymerase, respiratory enzymes, cytochrome oxidase, Krebs cycle enzymes, protein kinases, aminocyclopropane-1-carboxylic acid synthase, and enzymes involved in the shikimic acid pathway such as enolpyruvyl shikimic acid-5-phosphate synthase. The toxic product may either kill the plant cell in which it is expressed or simply disable the cell so that it is less capable of supporting the pathogen. It is preferred, particularly where the plant is a food plant, that the plant-toxic product be non-toxic to animals, and particularly be non-toxic to humans.

Alternatively, the nucleic acid molecule of the invention comprises a nematode-repressible promoter, more particularly the synthetic SCP1 promoter (SEQ ID NO:1), operably linked to a nematode-resistance inhibitor sequence. Nematode-repressible promoters provide a means for improved regulation of genetically engineered nematode resistance in plants. It is known that expression of a toxin gene product at nematode feeding sites can potentially harm uninfected plant cells in tissues adjacent to those sites. Thus, it can be beneficial to additionally alter the transgenic plant to express a product that counteracts excessive production of the toxin. See, for example, the methods disclosed in WO 92/21757. Thus, in another embodiment of the invention, the nematode-repressible promoter SCP1 (SEQ ID NO:1) is used in combination with a nematode-inducible promoter, such as the synthetic promoter UCP3 (SEQ ID NO:2) or SUP (SEQ ID NO:3), to effect improved regulation of nematode resistance in a plant. In this manner, two transgene units in one or two nucleic acid molecules are used in concert to transform plant cells and regenerate transgenic plants having improved nematode resistance with respect to nontransgenic plants of the same species. The first transgene unit comprises a nematode-inducible promoter, such as UCP3 or SUP, operably linked to a nematode-resistance sequence. Since SUP was found on average to have greater baseline levels of activity than UCP3, and since the activity varies with each transgenic event, the desired baseline level of each gene product will be important in determining which inducible promoter will be most useful in any given situation.

The second nucleic acid molecule comprises the nematode-repressible synthetic promoter SCP1 (SEQ ID NO:1) operably linked to a heterologous nucleotide sequence that encodes a gene product that, when expressed in a plant cell, inhibits or inactivates a toxic product of a nematode-resistance gene (i.e., that encoded by the first nucleic acid molecule) that has been engineered within the plant cell. Such products are referred to herein as "nematode-resistance inhibitor products," and their coding sequences are referred to herein as "nematode-resistance inhibitor sequences." In response to a nematode stimulus, expression of the nematode-resistance sequence allows for production of the toxin at the point of nematode invasion, while inhibition or repression of the expression of the nematode-resistance inhibitor product of the second nucleic acid molecule allows for the toxin to accumulate within the infected cells but not in the adjacent uninfected cells. Accordingly, in the absence of the nematode stimulus, such as in adjacent uninfected cells, expression of the inhibitor product of the second nucleic acid molecule protects against any aberrant accumulation of the toxin within these adjacent cells. Similarly, following removal of the nematode stimulus from an infected region, upregulation of expression of the inhibitor product encoded by the second nucleic acid molecule protects the remaining cells within the invasion region against the toxic effects of any residual toxin in these cells. SCP1 has strong and constitutive activity in various plant tissues (U.S. Pat. No. 6,072,050), but its activity can be significantly repressed in the nematode feeding sites. These features of SCP1 promoter make it a preferred choice for expressing a nematode-resistance inhibitor transgene in comparison with a constitutive promoter (WO 92/21757) in terms of improving nematode resistance. Examples of nematode-resistance inhibitor products whose expression is regulated by the nematode-repressible promoter include, but are not limited to, barstar, which neutralizes the activity of barnase; EcoRI methylase, which targets the endonuclease EcoRI; protease inhibitors targeting proteases, such as papain; and an antisense RNA complementary to a strand of sense RNA encoded by the toxic gene sequence in the first nucleic acid molecule.

Where the expression product (i.e., nematode-resistance product or nematode-resistance inhibitor product) is to be located in a cellular compartment other than the cytoplasm, the coding sequence may be constructed to include regions that code for particular amino acid sequences that result in translocation of the product to a particular site, such as the cell plasma membrane, or may be secreted into the periplasmic space or into the external environment of the cell. Various secretory leaders, membrane integration sequences, and translocation sequences for directing the peptide expression product to a particular site are described in the literature. See, for example, Cashmore et al., (1985) *Bio/Technology* 3:803–808 and Wickner and Lodish (1985) *Science* 230:400–407.

It is recognized that expression driven by pathogen-regulated promoter regions can be influenced by more than one pathogen or pest (see, for example, Strittmatter et al. (1996) *Mol. Plant Microb. Interact.* 9:68–73). Thus, in other embodiments of the invention, the nematode-regulated promoters SCP1, UCP3, and SUP can be used to create or enhance resistance of a plant to other pathogens or pests in accordance with the methods of the invention whenever infection by those pathogens or pests triggers enhanced or selective transcription from these promoters. Examples of such other pathogens include fungi, viruses, and bacteria, which are able to induce the promoter at their site of infection of the plant. In this manner, the nematode-inducible UCP3 or SUP promoters, or variants or fragments thereof, can be operably linked to a heterologous nucleotide sequence that encodes other pathogen-resistance sequences. By "pathogen-resistance" or "disease-resistance" it is intended that the plants avoid the disease symptoms that are the outcome of plant-pathogen interactions. That is, pathogens are prevented from causing plant diseases and the associated disease symptoms, or alternatively, the disease symptoms caused by the pathogen are minimized or lessened. Genes encoding disease resistance traits include, generally, detoxification genes, such as those against fumonisin (U.S. Pat. No. 5,792,931); avirulence (avr) and disease resistance (R) genes (Jones et al. (1994) *Science* 266:789; Martin et al. (1993) *Science* 262:1432; and Mindrinos et al. (1994) *Cell* 78:1089); and the like.

The nucleic acid molecules comprising a heterologous nucleotide sequence of interest, for example, a nematode-resistance sequence or nematode-resistance inhibitor sequence, operably linked to a nematode-regulated promoter of the invention can be provided in expression cassettes for expression in a plant of interest. Such an expression cassette is provided with a plurality of restriction sites for insertion of the nucleotide sequence to be under the transcriptional regulation of the nematode-regulated promoter region. The expression cassette may additionally contain selectable marker genes.

In order to increase transcription levels, enhancers may be utilized in combination with the promoter regions of the invention. Enhancers are nucleotide sequences that act to increase the expression of a promoter region. Enhancers are known in the art and include the SV40 enhancer region, the 35S enhancer element, and the like.

The expression cassette will include in the 5'-to-3' direction of transcription, a transcriptional and translational initiation region comprising the nematode-regulated SCP1, UCP3, or SUP promoter (or variant or fragment thereof), a heterologous nucleotide sequence of interest, and a transcriptional and translational termination region functional in plants. The termination region may be native with the transcriptional initiation region comprising one of the promoter nucleotide sequences of the present invention, may be native with the DNA sequence of interest, or may be derived from another source. Convenient termination regions are available from the Ti-plasmid of *A. tumefaciens*, such as the octopine synthase and nopaline synthase termination regions. See also, Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. 1989) *Nucleic Acids Res.* 17:7891–7903; Joshi et al. (1987) *Nucleic Acids Res.* 15:9627–9639.

The expression cassette comprising the SCP1, UCP3, or SUP promoter sequence (or variant or fragment thereof) operably linked to a heterologous nucleotide sequence of interest may also contain at least one additional nucleotide sequence for a gene to be cotransformed into the organism. Alternatively, the additional sequence(s) can be provided on another expression cassette.

Where appropriate, the heterologous nucleotide sequence of interest whose expression is to be under a control of a nematode-regulated promoter sequence described herein and any additional nucleotide sequence(s) may be optimized for increased expression in the transformed plant. That is, these nucleotide sequences can be synthesized using plant-preferred codons for improved expression. Methods are available in the art for synthesizing plant-preferred nucleotide sequences. See, for example, U.S. Pat. Nos. 5,380,831 and 5,436,391, and Murray et al. (1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the heterologous nucleotide sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include, but are not limited to: picomavirus leaders, for example, EMCV leader (Encephalomyocarditis 5' noncoding region) (Elroy-Stein et al. (1989) *Proc. Nat. Acad. Sci. USA* 86:6126–6130); potyvirus leaders, for example, TEV leader (Tobacco Etch Virus) (Allison et al. (1986) *Virology* 154:9–20); MDMV leader (Maize Dwarf Mosaic Virus); human immunoglobulin heavy-chain binding protein (BiP) (Macejak and Sarnow (1991) *Nature* 353:90–94); untranslated leader from the coat protein mRNA of alfalfa mosaic virus (AMV RNA 4) (Jobling and Gehrke (1987) *Nature* 325:622–625); tobacco mosaic virus leader (TMV) (Gallie et al. (1989) *Molecular Biology of RNA*, pages 237–256); and maize chlorotic mottle virus leader (MCMV) (Lommel et al. (1991) *Virology* 81:382–385). See also Della-Cioppa et al. (1987) *Plant Physiology* 84:965–968. Other methods known to enhance translation and/or mRNA stability can also be utilized, for example, introns, and the like.

In those instances where it is desirable to have the expressed product of the heterologous nucleotide sequence of interest directed to a particular organelle, such as the chloroplast or mitochondrion, or secreted at the cell's surface or extracellularly, the expression cassette may further comprise a coding sequence for a transit peptide. Such transit peptides are well known in the art and include, but are not limited to, the transit peptide for the acyl carrier protein, the small subunit of RUBISCO, plant EPSP synthase, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be performed to provide for convenient restriction sites, removal of superfluous DNA, removal of restriction sites, or the like. For this purpose, in vitro mutagenesis, primer repair, restriction, annealing, resubstitutions, for example, transitions and transversions, may be involved.

The nucleic acid molecules of the present invention are useful in methods directed to creating or enhancing pathogen-resistance, more particularly nematode resistance in a plant. Improved pathogen-resistance may be accomplished by stably transforming a plant of interest with a nucleic acid molecule that comprises a nematode-regulated promoter identified herein operably linked to a pathogen-resistance sequence to produce antipathogenic activity in such plants, or by the use of such transformed plants or other products to produce antipathogenic compositions. By "antipathogenic compositions" it is intended that the compositions have antipathogenic activity and thus are capable of suppressing, controlling, and/or killing the invading pathogenic organism. An antipathogenic composition will reduce the disease symptoms resulting from pathogen challenge by at least about 5% to about 50%, at least about 10% to about 60%, at least about 30% to about 70%, at least about 40% to about 80%, or at least about 50% to about 90% or greater. Hence, the methods of the invention can be utilized to protect plants from disease, particularly those diseases that are caused by plant pathogens. In a preferred embodiment, the pathogen-resistance sequence is a nematode-resistance sequence that, when expressed, produces a product that has antipathogenic properties for nematodes, and the nematode-regulated promoter is the nematode-inducible promoter UCP3 (SEQ ID NO:2) or SUP (SEQ ID NO:3). In another embodiment, the plant is cotransformed with a nucleic acid molecule comprising a nematode-repressible promoter, preferably the SCP1 promoter (SEQ ID NO:1) operably linked to a nematode-resistance inhibitor sequence as noted above.

Assays that measure antipathogenic activity are commonly known in the art, as are methods to quantitate disease resistance in plants following pathogen infection. See, for example, U.S. Pat. No. 5,614,395, herein incorporated by reference. Such techniques include, measuring over time, the average lesion diameter, the pathogen biomass, the overall percentage of decayed plant tissues, and nematode reproduction or size (Urwin et al. (1998) *Planta* 204: 472–479). For example, a plant either expressing an antipathogenic polypeptide or having an antipathogenic composition applied to its surface shows a decrease in tissue necrosis (i.e., lesion diameter) or a decrease in plant death following pathogen challenge when compared to a control plant that was not exposed to the antipathogenic composition. Alternatively, antipathogenic activity can be measured by a decrease in pathogen biomass. For example, a plant expressing an antipathogenic polypeptide or exposed to an antipathogenic composition is challenged with a pathogen of interest. Over time, tissue samples from the pathogen-inoculated tissues are obtained and RNA is extracted. The percent of a specific pathogen RNA transcript relative to the level of a plant specific transcript allows the level of pathogen biomass to be determined. See, for example, Thomma et al. (1998) *Plant Biology* 95:15107–15111, herein incorporated by reference.

Furthermore, in vitro antipathogenic assays include, for example, the addition of varying concentrations of the antipathogenic composition to paper disks and placing the disks on agar containing a suspension of the pathogen of interest. Following incubation, clear inhibition zones develop around the discs that contain an effective concentration of the antipathogenic polypeptide (Liu et al. (1994) *Plant Biology* 91:1888–1892, herein incorporated by reference). Additionally, microspectrophotometrical analysis can be used to measure the in vitro antipathogenic properties of a composition (Hu et al. (1997) *Plant Mol. Biol.* 34:949–959 and Cammue et al. (1992) *J. Biol. Chem.* 267: 2228–2233, both of which are herein incorporated by reference).

Also contemplated are antipathogenic assays directed at nematode pathogens. Such assays are known to the skilled artisan, and may include assays directed at specific characteristics of nematode pathogen infections, such as assays directed at nematode feeding site formation. Such assays include those disclosed in U.S. Pat. Nos. 6,008,436; and 6,252,138; herein incorporated by reference.

In addition to being used singly, the pathogen-resistance sequences, more particularly the nematode-resistance sequences, described herein may be used in combination with sequences encoding other proteins or agents to protect against plant diseases and pathogens. Other plant defense proteins include those described in the copending application entitled "Methods for Enhancing Disease Resistance in Plants", U.S. application Ser. No. 09/256,898, filed Feb. 24, 1999, herein incorporated by reference.

Fragments and variants of the SCP1, UCP3, or SUP promoter sequences can be used in the compositions and methods of the present invention. By "fragment" a portion of the promoter nucleotide sequence that retains its nematode-regulated activity is intended. Thus, for example, less than the entire sequence set forth in SEQ ID NO:1, 2, or 3 may be utilized to drive expression of an operably linked heterologous nucleotide sequence of interest, such as a nucleotide sequence encoding a nematode-resistance protein or polypeptide. It is within skill in the art to determine whether such fragments decrease expression levels or alter the nature of expression, i.e., nematode-inducible or nematode repressible expression. Based on the comparison of the sequence among CaMV 35S and SCP1 (see FIG. 1), the UAR of the CaMV 35S promoter (designated 35SUAR herein) contains DNA elements that down-regulate promoter activity in response to a nematode stimulus. In contrast, the UAR of the maize ubiquitin-1 promoter (designated UbiUAR herein) have DNA elements that up-regulate promoter activity in response to a nematode stimulus. When both the 35SUAR containing the Rysn7 element and the UbiUAR are placed adjacent to each other and operably linked to the Rysn7-SynII core promoter, the resultant promoter retains the inducible property that is characteristic of the UbiUAR in response to a nematode stimulus.

Thus, the 35SUAR and UbiUAR sequences comprise nematode-responsive cis-acting elements. By "nematode-responsive cis-acting elements" nucleotide sequences present in the 35SUAR or UbiUAR that cause an operably linked promoter sequence to up-regulate or down-regulate transcription of an operably-linked sequence of interest in response to a nematode stimulus is intended. The nematode-responsive cis-acting elements can be as small as 4 or 6 basepairs, and can modify nematode-regulated activity of other promoters by cloning one or more copies of these elements into these promoters as described herein below.

Suitable nucleotide sequences that are transcriptionally active fragments of a nematode-resistance promoter comprise at least 4, 6, 10, 20, 30, 40, 50, 60, 70, 80, 90, 100, 200, 300, 325, 350, 375, 400, 425, 450, 500, 550, 600, 650, 700, 800, 900, 1000, 1100, 1200, 1300, 1400, 1500, 1600, 1700, 1800, 1900, 2000, 2100, 2200, 2300, 2400, 2500, or 2600 nucleotides, or up to the number of nucleotides present in the full-length promoter nucleotide sequence disclosed herein (i.e., 485 nucleotides for SEQ ID NO:1, 2609 nucleotides for SEQ ID NO:2, and 1413 nucleotides for SEQ ID NO:3). Such fragments retain their nematode-regulated activity. Preferred fragment lengths depend upon the objective and will also vary depending upon the particular promoter sequence.

The nucleotides of such fragments will comprise the TATA recognition sequence of the particular promoter sequence and preferably either the UAR sequence, i.e., the 35SUAR sequence or the UAR sequence (−876 to −55) of the ubiquitin-1 promoter from *Zea mays* (i.e., UbiUAR) or both. Such fragments may be obtained by use of restriction enzymes to cleave the SCP1, UCP3, or SUP promoter nucleotide sequence disclosed herein; by synthesizing a nucleotide sequence from the SCP1, UCP3, or SUP promoter DNA sequence; or through the use of PCR technology. See particularly, Mullis et al. (1987) *Methods Enzymol.* 155:335–350, and Erlich, ed. (1989) *PCR Technology* (Stockton Press, New York). Variants of these promoter fragments, such as those resulting from site-directed mutagenesis, are also encompassed by the compositions of the present invention.

Thus, suitable promoter fragments or variants retain functional promoter activity, that is, the fragments or variants obtained are capable of directing RNA polymerase II to initiate RNA synthesis at the appropriate transcription initiation site for a particular coding sequence in response to a nematode stimulus where the promoter is nematode-inducible or direct transcription in the absence of the nematode stimulus in the case of a nematode-repressible promoter. A variety of assays are known for measuring such activity, including assaying the production of RNA transcripts by, for example, Northern blot hybridization. Alternatively, levels of a reporter gene such as green fluorescent protein (GFP) or the like produced under the control of a promoter fragment or variant can be measured. See, for example, U.S. Pat. No. 6,072,050, herein incorporated by reference.

By "variants" promoter sequences having substantial similarity with a synthetic promoter sequence disclosed herein are intended. Generally, variants of a particular nucleotide sequence of the invention will have at least about 40%, 50%, 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to that particular nucleotide sequence as determined by sequence alignment programs described elsewhere herein using default parameters. Such variants retain the nematode-regulated promoter activity of the disclosed promoter sequences. Thus variants of the SCP1 sequence retain nematode-repressible promoter activity, and variants of the UCP3 and SUP sequences retain nematode-inducible promoter activity.

The variant promoter sequences will share substantial homology with their corresponding synthetic promoter sequence. By "substantial homology" a sequence exhibiting substantial functional and structural equivalence with the disclosed sequence is intended. Any functional or structural differences between substantially homologous sequences do not effect the ability of the sequence to function as a nematode-regulated promoter. Thus, for example, any sequence having substantial sequence homology with the sequence of a particular nematode-inducible promoter of the present invention will direct expression of an operably linked heterologous nucleotide sequence in response to a nematode stimulus. Two nucleotide sequences are considered substantially homologous when they have at least about 50%, 60%, to 70%, generally at least about 80%, preferably at least about 85%, 90%, to 98% sequence homology. Substantially homologous sequences of the present invention include variants of the disclosed sequences such as those that result from site-directed mutagenesis, as well as synthetically derived sequences.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) CABIOS 4:11–17; the local homology algorithm of Smith et al. (1981) Adv. Appl. Math. 2:482; the homology alignment algorithm of Needleman and Wunsch (1970) J. Mol. Biol. 48:443–453; the search-for-similarity-method of Pearson and Lipman (1988) Proc. Natl. Acad. Sci. 85:2444–2448; the algorithm of Karlin and Altschul (1990) Proc. Natl. Acad. Sci. USA 872264, and modified as in Karlin and Altschul (1993) Proc. Natl. Acad. Sci. USA 90:5873–5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) Gene 73:237–244 (1988); Higgins et al. (1989) CABIOS 5:151–153; Corpet et al. (1988) Nucleic Acids Res. 16:10881–90; Huang et al. (1992) CABIOS 8:155–65; and Pearson et al. (1994) Meth. Mol. Biol. 24:307–331. The ALIGN program is based on the algorithm of Myers and Miller (1988) supra. The BLAST programs of Altschul et al (1990) J. Mol. Biol. 215:403 are based on the algorithm of Karlin and Altschul (1990) supra. BLAST nucleotide searches can be performed with the BLASTN program, score=100, wordlength=12, to obtain nucleotide sequences homologous to a synthetic promoter nucleotide sequence disclosed herein. To obtain gapped alignments for comparison purposes, Gapped BLAST (in BLAST 2.0) can be utilized as described in Altschul et al. (1997) Nucleic Acids Res. 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences) can be used. Alignment may also be performed manually by inspection.

Unless otherwise stated, sequence identity/similarity values provided herein refer to the value obtained using GAP version 10 using the following parameters: % identity using a GAP Weight of 50 and a Length Weight of 3; % similarity using a Gap Weight of 12 and a Length Weight of 4, or any equivalent program. By "equivalent program any sequence comparison program that, for any two sequences in question, generates an alignment having identical nucleotide matches and an identical percent sequence identity when compared to the corresponding alignment generated by GAP Version 10" is intended.

GAP uses the algorithm of Needleman and Wunsch (1970) J. Mol. Biol. 48: 443–453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the Quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two nucleic acid sequences makes reference to the bases in the two sequences that are the same when aligned for maximum correspondence over a specified comparison window.

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison, and multiplying the result by 100 to yield the percentage of sequence identity.

(e) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters.

Another indication that nucleotide sequences are substantially identical is if two molecules hybridize to each other under stringent conditions. By "stringent conditions" or "stringent hybridization conditions" conditions under which a probe will hybridize to its target sequence to a detectably greater degree than to other sequences (e.g., at least 2-fold over background) are intended. Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. The $T_m$ (thermal melting point) is the temperature (under defined ionic strength and pH) at which 50% of a complementary target sequence hybridizes to a perfectly matched probe. For DNA-DNA hybrids, the $T_m$ can be approximated from the equation of Meinkoth and Wahl (1984) *Anal. Biochem.* 138:267–284: $T_m$=81.5° C.+16.6 (log M)+0.41 (% GC)–0.61 (% form)–500/where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$).

Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al, Eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C. lower than the $T_m$, depending upon the desired degree of stringency as otherwise qualified herein.

Thus, isolated sequences that encode for a promoter and which hybridize under stringent conditions to the nematode-regulated promoters disclosed herein, or to fragments thereof, are encompassed by the present invention. Such sequences will be at least about 40% to 50% homologous, about 60%, 65%, or 70% homologous, and even at least about 75%, 80%, 85%, 90%, 91%, 92%, 93%, 94%, 95%, 96%, 97%, 98%, 99%, or more homologous wit the disclosed sequences. That is, the sequence identity of sequences may range, sharing at least about 40% to 50%, about 60%, 65%, or 70%, and even at least about 75%, 80%, 85%, 90%, 91%, 92%, 93%, 94%, 95%, 96%, 97%, 98%, 99%, or more sequence identity.

Having identified the 35SUAR and UbiUAR as comprising nematode-responsive cis-acting elements that influence the responsiveness of a particular promoter to a nematode stimulus, it is possible to use these UARs, or fragments or variants of these UARs that retain the respective nematode-responsive cis-acting elements, to generate other nematode-regulated promoters. Thus, the present invention provides a method for preparing a nematode-regulated promoter using any promoter of interest that is capable of driving expression of an operably linked sequence. The method comprises modifying the promoter of interest to comprise at least one copy of at least one sequence selected from the group consisting of the 35SUAR (SEQ ID NO:4), the UbiUAR (SEQ ID NO:5), and variants or fragments of these UARs that retain the respective nematode-responsive cis-acting element or elements that are responsible for triggering up-regulation (in the case of a nematode-inducible element) or down-regulation (in the case of a nematode-repressible element) of expression of an operably linked nucleotide sequence in response to a nematode stimulus. Thus, the promoter can be modified to comprise at least one copy of 35SUAR or variant thereof and/or at least one copy of UbiUAR or variant thereof, at least one copy of a fragment of 35SUAR that comprises a nematode-responsive cis-acting element of 35SUAR and/or at least one copy of a fragment of UbiUAR that comprises a nematode-responsive cis-acting element of UbiUAR; and any combination thereof. Thus, for example, a promoter can be modified to comprise at least one copy of the complete 35SUAR or variant thereof and at least one copy of a fragment of UbiUAR that comprises a nematode-responsive cis-acting element of UbiUAR. Alternatively, a promoter can be modified to comprise at least one copy of a fragment of 35SUAR that comprises a nematode-responsive cis-acting element of 35SUAR and at least one copy of the complete UbiUAR or variant thereof. As nematode-responsive cis-acting elements can be as small as 4 to 6 basepairs, fragments of 35SUAR or UbiUAR that comprise a nematode-responsive cis-acting element can be as small as 4 to 6 basepairs of 35SUAR (SEQ ID NO:4) or 4 to 6 basepairs of UbiUAR (SEQ ID NO:5). When multiple copies are utilized, they can be tandem repeats of one of these UARs, tandem repeats of variants or fragments of these UARs, or various combinations of these UARs, their variants, and their fragments, where the variants and fragments comprise a nematode-responsive cis-acting element of these UARs.

Promoters that have been modified in accordance with this method of the invention can be operably linked to a heterologous nucleotide sequence as noted elsewhere herein and used in the transformation methods of the invention to provide for enhanced nematode and pathogen resistance in any plant of interest.

In preparing these nematode-regulated promoters, the various DNA sequences may be manipulated so as to provide for DNA sequences in the proper orientation, and as appropriate in the proper reading frame. The various UARs or fragments thereof comprising the nematode-responsive cis-acting elements may be introduced into a particular DNA construct consecutively by restriction enzyme cleavage of an appropriate replication system comprising this construct. After ligation and cloning, the DNA construct may be isolated for further manipulation. All of these techniques are amply exemplified in the literature and find particular exemplification in Sambrook et al. (1989) *Molecular Cloning: A Laboratory Manual* (2d ed., Cold Spring Harbor Laboratory Press, Plainview, N.Y.).

In the transformation methods of the present invention, a nematode-regulated promoter, i.e., SCP1, UCP3, SUP, or a promoter modified to comprise at least one copy of at least one sequence selected from the 35SUAR or the UbiUAR, or variant or fragment thereof, operably linked to a heterologous nucleotide sequence of interest can be used to stably transform any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*)), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga*

*menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Preferably, plants of the present invention are crop plants (for example, corn, alfalfa, sunflower, *Brassica*, soybean, cotton, safflower, peanut, sorghum, wheat, millet, tobacco, etc.), more preferably corn and soybean plants, yet more preferably corn plants.

Plants of particular interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

Other plants of interest that are susceptible to diseases caused by nematodes, and the corresponding nematodes of interest include: alfalfa: *Ditylenchus dipsaci, Meloidogyne hapla, Meloidogyne incognita, Meloidogyne javanica, Pratylenchus*spp., *Paratylenchus* spp., *Xiphinema* spp.; banana: *Radopholus similis, Helicotylenchus multicinctus, Meloidogyne incognita, M. arenaria, M. javanica, Pratylenchus coffeae, Rotylenchulus reniformis*; beans & peas: *Meloidogyne* spp., *Heterodera* spp., *Belonolaimus* spp., *Helicotylenchus* spp., *Rotylenchulus reniformis, Paratrichodorus anemones, Trichodorus* spp.; cassava: *Rotylenchulus reniformis, Meloidogyne* spp.; cereals: *Anguina tritici* (Emmer, rye, spelt wheat), *Bidera avenae* (oat, wheat), *Ditylenchus dipsaci* (rye, oat), *Subanguina radicicola* (oat, barley, wheat, rye), *Meloidogyne naasi* (barley, wheat, rye), *Pratylenchus* spp. (oat, wheat, barley, rye), *Paratylenchus* spp. (wheat), *Tylenchorhynchus* spp. (wheat, oat); chickpea: *Heterodera cajani, Rotylenchulus reniformis, Hoplolaimus seinhorsti, Meloidogyne* spp., *Pratylenchus* spp.; citrus: *Tylenchulus semipenetrans, Radopholus similis, Radopholus citrophilus* (Florida only), *Hemicycliophora arenaria, Pratylenchus* spp., *Meloidogyne* spp., *Bolonolaimus longicaudatus* (Florida only), *Trichodorus, Paratrichodorus, Xiphinema* spp.; clover: *Meloidogyne* spp., *Heterodera trifoli*; coconut: *Rhadinaphelenchus cocophilus*; coffee: *Meloidogyne incognita* (most important in Brazil), *M. exigua* (widespread), *Pratylenchus coffeae, Pratylenchus brachyurus, Radopholus similis, Rotylenchulus reniformis, Helicotylenchus* spp.; corn: *Pratylenchus* spp., *Paratrichodorus minor, Longidorus* spp., *Hoplolaimus columbus*; cotton: *Meloidogyne incognita, Belonolaimus longicaudatus, Rotylenchulus reniformis, Hoplolaimus galeatus, Pratylenchus* spp., *Tylenchorhynchus* spp., *Paratrichodorus minor*; grapes: *Xiphinema* spp., *Pratylenchus vulnus, Meloidogyne* spp., *Tylenchulus semipenetrans, Rotylenchulus reniformis*; grasses: *Pratylenchus* spp., *Longidorus* spp., *Paratrichodorus christiei, Xiphinema* spp., *Ditylenchus* spp.; peanut: *Pratylenchus* spp., *Meloidogyne hapla., Meloidogyne arenaria, Criconemella* spp., *Belonolaimus longicaudatus* (in Eastern United States); pigeonpea: *Heterodera cajani, Rotylenchulus reniformis, Hoplolaimus seinhorsti, Meloidogyne* spp., *Pratylenchus* spp.; pineapple: *Paratrichodorus christiei, Criconemella* spp., *Meloidogyne* spp., *Rotylenchulus reniformis, Helicotylenchus* spp., *Pratylenchus* spp., *Paratylenchus* spp.; potato: *Globodera rostochiensis, Globodera pallida, Meloidogyne* spp., *Pratylenchus* spp., *Trichodorus primitivus, Ditylenchus* spp., *Paratrichodorus* spp., *Nacoabbus aberrans*; rice: *Aphelenchiodes besseyi, Ditylenchus angustus, Hirchmanniella* spp., *Heterodera oryzae, Meloidogyne* spp.; small fruits: *Meloidogyne* spp., *Pratylenchus* spp., *Xiphinema* spp., *Longidorus* spp., *Paratrichodorus christiei, Aphelenchoides* spp. (strawberry); soybean: *Heterodera glycines, Meloidogyne incognita, Meloidogyne javanica, Belonolaimus* spp., *Hoplolaimus columbus*; sugar beet: *Heterodera schachtii, Ditylenchus dipsaci, Meloidogyne* spp., *Nacobbus aberrans, Trichodorus* spp., *Longidorus* spp., *Paratrichodorus* spp.; sugar cane: *Meloidogyne* spp., *Pratylenchus* spp., *Radopholus* spp., *Heterodera* spp., *Hoplolaimus* spp., *Helicotylenchus* spp., *Scutellonema* spp., *Belonolaimus* spp., *Tylenchorhynchus* spp., *Xiphinema* spp., *Longidorus* spp., *Paratrichodorus* spp.; tea: *Meloidogyne* spp., *Pratylenchus* spp., *Radopholus similis, Hemicriconemoides kanayaensis, Helicotylenchus* spp., *Paratylenchus curvitatus*; tobacco: *Meloidogyne* spp., *Pratylenchus* spp., *Tylenchorhynchus claytoni, Globodera tabacum, Trichodorus* spp., *Xiphinema americanum, Ditylenchus dipsaci* (Europe only), *Paratrichodorus* spp.; tomato: *Pratylenchus* spp., *Meloidogyne* spp.; tree fruits: *Pratylenchus* spp. (apple, pear, stone fruits), *Paratylenchus* spp. (apple, pear), *Xiphinema* spp. (pear, cherry, peach), *Cacopaurus pestis* (walnut), *Meloidogyne* spp. (stone fruits, apple, etc.), *Longidorus* spp. (cherry), *Criconemella* spp. (peach), and *Tylenchulus* spp. (olive).

The present invention is directed towards the transformation of plants with nucleotide constructs. The use of the term "nucleotide constructs" herein is not intended to limit the present invention to nucleotide constructs comprising DNA. Those of ordinary skill in the art will recognize that nucleotide constructs, particularly polynucleotides and oligonucleotides, comprised of ribonucleotides and combinations of ribonucleotides and deoxyribonucleotides may also be employed in the methods disclosed herein. Thus, the nucleotide constructs of the present invention encompass all nucleotide constructs that can be employed in the methods of the present invention for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs of the invention also encompass all forms of nucleotide constructs including, but not limited to, single-stranded forms, double-stranded forms, hairpins, stem-and-loop structures, and the like.

Furthermore, it is recognized that the methods of the invention may employ a nucleotide construct that is capable of directing, in a transformed plant, the expression of at least one protein, or at least one RNA, such as, for example, an antisense RNA that is complementary to at least a portion of an mRNA. Typically such a nucleotide construct is comprised of a coding sequence for a protein or an RNA operably linked to 5' and 3' transcriptional regulatory regions. Alternatively, it is also recognized that the methods of the invention may employ a nucleotide construct that is not capable of directing, in a transformed plant, the expression of a protein or an RNA.

In addition, it is recognized that methods of the present invention do not depend on the incorporation of the entire nucleotide construct into the genome, only that the plant or cell thereof is altered as a result of the introduction of the nucleotide construct into a cell. In one embodiment of the invention, the genome may be altered following the introduction of the nucleotide construct into a cell. For example, the nucleotide construct, or any part thereof, may incorporate into the genome of the plant. Alterations to the genome of the present invention include, but are not limited to, additions, deletions, and substitutions of nucleotides in the genome. While the methods of the present invention do not depend on additions, deletions, or substitutions of any particular number of nucleotides, it is recognized that such additions, deletions, or substitutions comprise at least one nucleotide.

As used herein, "vector" refers to a DNA molecule such as a plasmid, cosmid or bacterial phage for introducing a nucleotide construct into a host cell. Cloning vectors typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance, or ampicillin resistance.

The methods of the invention involve introducing a nucleotide construct into a plant. By "introducing" presenting to the plant the nucleotide construct in such a manner that the construct gains access to the interior of a cell of the plant is intended. The methods of the invention do not depend on a particular method for introducing a nucleotide construct to a plant, only that the nucleotide construct gains access to the interior of at least one cell of the plant. Methods for introducing nucleotide constructs into plants are known in the art including, but not limited to, stable transformation methods, transient transformation methods, and virus-mediated methods.

By "stable transformation" it is intended that the nucleotide construct introduced into a plant integrates into the genome of the plant and is capable of being inherited by progeny thereof. By "transient transformation" it is intended that a nucleotide construct introduced into a plant does not integrate into the genome of the plant.

The nucleotide constructs of the invention may be introduced into plants by contacting plants with a virus or viral nucleic acids. Generally, such methods involve incorporating a nucleotide construct of the invention within a viral DNA or RNA molecule. It is recognized that the pathogen-resistance protein of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing nucleotide constructs into plants and expressing a protein encoded therein, involving viral DNA or RNA molecules, are known in the art. See, for example, U.S. Pat. Nos. 5,889,191, 5,889,190, 5,866,785, 5,589,367 and 5,316,931; herein incorporated by reference.

A variety of other transformation protocols are contemplated in the present invention. Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, *Agrobacterium*-mediated transformation (U.S. Pat. Nos. 5,563,055 and 5,981,840), direct gene transfer (Paszkowski et al. (1984) *EMBO J.* 3:2717–2722), and ballistic particle acceleration (see, for example, U.S. Pat. Nos. 4,945,050; 5,879,918; 5,886,244; 5,932,782; and Tomes et al. (1995) "Direct DNA Transfer into Intact Plant Cells via Microprojectile Bombardment," in *Plant Cell, Tissue, and Organ Culture: Fundamental Methods*, Eds. Gamborg and Phillips (Springer-Verlag, Berlin); and McCabe et al. (1988) *Biotechnology* 6:923–926), and Lec1 transformation (WO 00/28058 published May 18, 2000. Also see, Weissinger et al. (1988) *Ann. Rev. Genet.* 22:421–477; Sanford et al. (1987) *Particulate Science and Technology* 5:27–37 (onion); Christou et al. (1988) *Plant Physiol.* 87:671–674 (soybean); Finer and McMullen (1991) *In Vitro Cell Dev. Biol.* 27P:175–182 (soybean); Singh et al. (1998) *Theor. Appl. Genet.* 96:319–324 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); U.S. Pat. Nos. 5,240,855; 5,322,783 and 5,324,646; Klein et al. (1988) *Plant Physiol.* 91:440–444 (maize); Fromm et al. (1990) *Biotechnology* 8:833–839 (maize); Hooykaas-Van Slogteren et al. (1984) *Nature (London)* 311:763–764; Bowen et al., U.S. Pat. No. 5,736,369 (cereals); Bytebier et al. (1987) *Proc. Natl. Acad Sci. USA* 84:5345–5349 (Liliaceae); De Wet et al. (1985) in *The Experimental Manipulation of Ovule Tissues*, ed. Chapman et al. (Longman, New York), pp. 197–209 (pollen); Kaeppler et al. (1990) *Plant Cell Reports* 9:415–418 and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference.

The present invention contemplates the use of selectable marker genes for the selection of transformed cells or tissues. Thus, generally, the expression cassette will comprise a selectable marker gene for the selection of transformed cells. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate, glyphosate, bromoxynil, imidazolinones, and 2,4-dichlorophenoxyacetate (2,4-D). See generally, Yarranton (1992) *Curr. Opin. Biotech.* 3:506–511; Christopherson et al. (1992) *Proc. Natl. Acad. Sci. USA* 89:6314–6318; Yao et al (1992) *Cell* 71:63–72; Reznikoff (1992) *Mol. Microbiol.*, 6:2419–2422; Barkley et al. (1980) in *The Operon*, pp. 177–220; Hu et al. (1987) *Cell* 48:555–566; Brown et al. (1987) *Cell* 49:603–612; Figge et al. (1988) *Cell* 52:713–722; Deuschle et al. (1989) *Proc. Natl. Acad. Aci. USA* 86:5400–5404; Fuerst et al. (1989) *Proc. Natl. Acad Sci. USA* 86:2549–2553; Deuschle et al. (1990) *Science* 248:480–483; Gossen (1993) Ph.D. Thesis, University of Heidelberg; Reines et al. (1993) *Proc. Natl. Acad Sci. USA* 90:1917–1921; Labow et al. (1990) *Mol. Cell. Biol.* 10:3343–3356; Zambretti et al. (1992) *Proc. Natl. Acad Sci. USA* 89:3952–3956; Baim et al. (1991) *Proc. Natl. Acad Sci. USA* 88:5072–5076; Wyborski et al. (1991) *Nucleic Acids Res.* 19:4647–4653; Hillenand-Wissman (1989) *Topics Mol. Struc. Biol.* 10:143–162; Degenkolb et al. (1991) *Antimicrob. Agents Chemother.* 35:1591–1595; Kleinschnidt et al (1988) *Biochemistry* 27:1094–1104; Bonin (1993) Ph.D. Thesis, University of Heidelberg; Gossen et al. (1992) *Proc. Natl. Acad Sci. USA* 89:5547–5551; Oliva et al. (1992) *Antimicrob. Agents Chemother.* 36:913–919; Hlavka et al. (1985) *Handbook of Experimental Pharmacology*, Vol. 78 (Springer-Verlag, Berlin); Gill et al. (1988) *Nature* 334: 721–724 and U.S. patent application Ser. No. 10/072,307. Such disclosures are herein incorporated by reference. This list of selectable marker genes is not meant to be limiting. Any selectable marker gene can be used in the present invention. Alternatively, nematode-resistance may be directly selected by inoculating nematodes into the transformed protoplasts, cells, or tissues. Both methods of selection are generally known in the art.

The cells that have been transformed may be grown into plants in accordance with conventional ways. See, for example, McCormick et al. (1986) *Plant Cell Reports* 5:81–84. These plants may then be grown, and either pollinated with the same transformed strain or different strains, and the resulting hybrids having nematode-regulated expression of the desired phenotypic characteristic identified, i.e., enhanced nematode resistance relative to a non-transformed plant of the representative species of interest. Two or more generations may be grown to ensure that expression of the desired phenotypic characteristic is stably maintained and inherited and then seeds harvested to ensure expression of the desired phenotypic characteristic has been achieved. Thus as used herein, "transformed seeds" refers to seeds that contain the nucleotide construct stably integrated into the plant genome.

The following illustrative examples are presented to illustrate embodiments of the present invention, and are not meant to limit the scope of the invention unless otherwise specified.

Experimental

The following stock solutions and media were used for transformation and regeneration of soybean roots:

| Stock Solutions: | |
|---|---|
| 10 X B-5 Majors: | 25.00 g $KNO_3$, 1.34 g $(NH_4)_2 SO_4$, 2.50 g $MgSO_4.7H_2O$, 1.50 g $CaCl_2 2H_2O$, 1.31 g $NaH_2PO_4$ (anhydrous). |
| 100 X B-5 Minors: | 1.00 g $MnSO_4.H_2O$, 0.30 g $H_3BO_3$, 0.20 g $ZnSO_4.7H_2O$, 0.075 g KI. |
| 100 X B-5 Vitamins with Thiamin: | 10.00 g myo-Inositol, 1.00 g Thiamine*HCl, 0.10 g Nicotinic acid, 0.10 g Pyridoxine HCl. |
| 100 X Iron Mix: | 3.73 g. $Na_2EDTA$, 2.78 g $FeSO_4.7H2O$. |
| Media (per Liter): | |
| Minimal A medium: | 10.5 g $K_2HPO_4$, 4.5 g $KH_2PO_4$, 1.0 g $(NH_4)_2SO_4$, 0.5 g $(Na)_2C_6H_5O_7.2H_2O$, 246.5 mg $MgSO_4$ $7H_2O$, 2 g sucrose, 15 g agar. |
| 0 B-5 medium: | 0.6 g MES [2-(N-Morpholino) ethane-sulfonic acid (Sigma, M5287), 20 g sucrose, 10 ml 100X B-5 minors, 100 ml 10X B-5 majors, 10 ml 100X B-5 vitamins with Thiamine, 10 ml 100X Iron mix. |
| MXB medium: | Murashige and Skoog Basal nutrient salts (M5524, Sigma), 1 X B-5 Vitamins with thiamine, 30 g sucrose, 3 g gelrite, pH 5.7. |

EXAMPLE 1

Generation of Soybean Transgenic Hairy Roots

*Agrobacterium rhizogenes* strain K599 was grown and maintained on LB, minimal A, or yeast extract and peptone (YEP) media. Soybean seeds were surface-sterilized by setting in chlorine gas under controlled conditions for 12–16 hours, and then aerating in a clean air hood for at least 30 min. Seeds were germinated and cultured in Magenta™ boxes (Magenta Corp.) containing sterile potting soil and 10 to 15 ml of 25% Gamborg's B-5 Basal medium with minimal organics (Sigma) at 26° C. with a 16 hour photoperiod provided by fluorescent light.

The hypocotyl or cotyledons of 6-days-old seedlings were wounded using a 1 ml syringe with 21 gauge needle and injecting the bacteria or using a sterile scalpel dipped in a freshly grown culture of *A. rhizogenes* containing the construct. Hypocotyls just under the cotyledons were wounded 4 to 6 times in the epidermal cell layer. Cotyledons were inoculated by uniformly wounding the abaxial face several times. Plants and cotyledons were cultured under the same conditions used for seed germination.

Adventitious soybean roots were excised from soybean hypocotyls or cotyledons inoculated with *A. rhizogenes*. Initially these putative transformed roots were cultured in liquid 0 B-5 medium with antibiotics to cure the roots of any associated bacteria. Transfers of roots in liquid 0 B-5 were conducted every 2–3 days for three transfers. After the third root transfer in liquid 0 B-5, each root was transferred to a plate of Gamborg's B-5 agar with 0.5% Noble agar, pH 5.7 or MXB media (MS basal nutrient salts, B5 vitamins, and 3% sucrose (pH 5.7)+3 g/l Gelrite). Cultured roots were maintained in an incubator, without light, set at 24–30° C. Kanamycin (150 µg/ml) was added to the MXB medium to test kanamycin sensitivity of soybean roots. Roots were maintained on Gamborg's B-5 agar or MXB media. A 1–4 cm piece of root tip was excised and transferred to fresh medium every 2–4 weeks.

EXAMPLE 2

SCN Infection Assay

Roots for SCN bioassay were transferred to 6-cell plates of Gamborg's B-5 medium or MXB medium with 0.8% Daishiin agar (pH 6.5) 4–10 days before inoculation with second-stage juveniles of SCN. Two to five root tips were placed in each cell. Four of the six cells were used for testing transformed roots for reaction to SCN, one cell contained an untransformed SCN-susceptible control, and one cell contained an untransformed SCN-resistant control. The transformed roots were inoculated by placing 500 second stage juveniles of SCN race 3 directly on the roots in each cell and incubated for 7 days at 26–28° C.

EXAMPLE 3

Quantitative GUS Analysis

Soybean roots were homogenized in tubes containing 400 µl of extraction buffer (50 mM $K_2HPO_4$, pH 7.8, 10 mM EDTA, 1 mM DTT). Samples were centrifuged at 5000 g for 10 min and supernatants were collected for GUS assay. Protein concentration was measured using Protein Assay kit from (Bio-Rad). GUS assay was carried out using GUS-Light™ kit (TROPIX) according to manufacturer's protocol.

EXAMPLE 4

Histochemical Analysis of GUS Expression in SCN Syncytium

Root samples were infected with SCN and collected at different time points after inoculation. These samples were fixed in 0.1% glutaraldehyde in 25 mM phosphate buffer and infiltrated using a vacuum at 15 psi for 2 min. After washing in 25 mM phosphate buffer, root samples were immersed in GUS staining solution (0.05% 5-bromo-4-4chloro-indolyl-β-D-glucturonide in 100 mM sodium phosphate buffer, pH 7.0, containing 10 mM EDTA, 0.1% Triton, and 0.5 mM K$_4$Fe(CN) 6H$_2$O) and infiltrated for 2 min at 15 psi. The GUS staining was continued at 37° C. for 12 hours. Root samples were then boiled in acid fuschin solution for 2 minutes and de-stained in acidic glycerin (100 ml of glycerin and 500 ul of HCI). Samples were examined under a dissecting microscope for SCN-hairy root interaction and GUS expression patterns. Dissected root segments for thin section were fixed in 3% glutaraldehyde in 25 mM phosphate buffer for 2 hours, and washed three times in 25 mM phosphate buffer for 30 min. Two different section methods were used to prepare each section. For analysis of SCP1: GUS events, a three-step buffer exchange was carried out to replace ethanol with L.R. white resin (3:1; 1:1; and 1:3, ethanol 100: L.R. white resin). Roots were thin-sectioned (2 μm) with a Leica microtone.

For UCP3 events, root tissues were dehydrated through an ethanol series of 30%, 50%, 70% 95%, and three changes in 100%, 30 min per change. A gradual buffer exchange was carried out to replace enthanol with Histoclear (100%), and then with paraffin at 60° C. Roots were thin-sectioned (10 μm) with a Leica microtome, and whole root samples or thin sections were examined under dissecting and light microscopy.

EXAMPLE 5

SCP1 Promoter Activity in Soybean Hairy Roots

The SCP1 promoter directed GUS expression to a level of about 5,000 GUS units/μg protein in uninfected transgenic soybean hairy roots. Additionally, this promoter exhibited strong activity in various root tissues including cortex, pericycle, and vascular cylinder of uninfected and early infected roots (one week after infection). However, SCP1 promoter activity in some feeding sites significantly reduced with the development of the feeding sites. A total of 60 feeding sites were examined under the microscope 4-weeks after inoculation. Forty-eight of them showed the same level of GUS expression as the control. Ten of them exhibited a reduction of GUS levels by 30–50% relative to the control. Two of the feeding sites showed near complete GUS suppression.

EXAMPLE 6

UCP3 Promoter Activity in Soybean Hairy Roots

The UCP3 promoter directed GUS expression in uninfected transgenic soybean hairy roots to a level of about ½₀ that of the SCP1 promoter. This activity was significantly induced in the feeding sites, as judged by microscopic examination of the feeding sites.

EXAMPLE 7

SUP Promoter Activity in Soybean Hairy Roots

Figure 2:
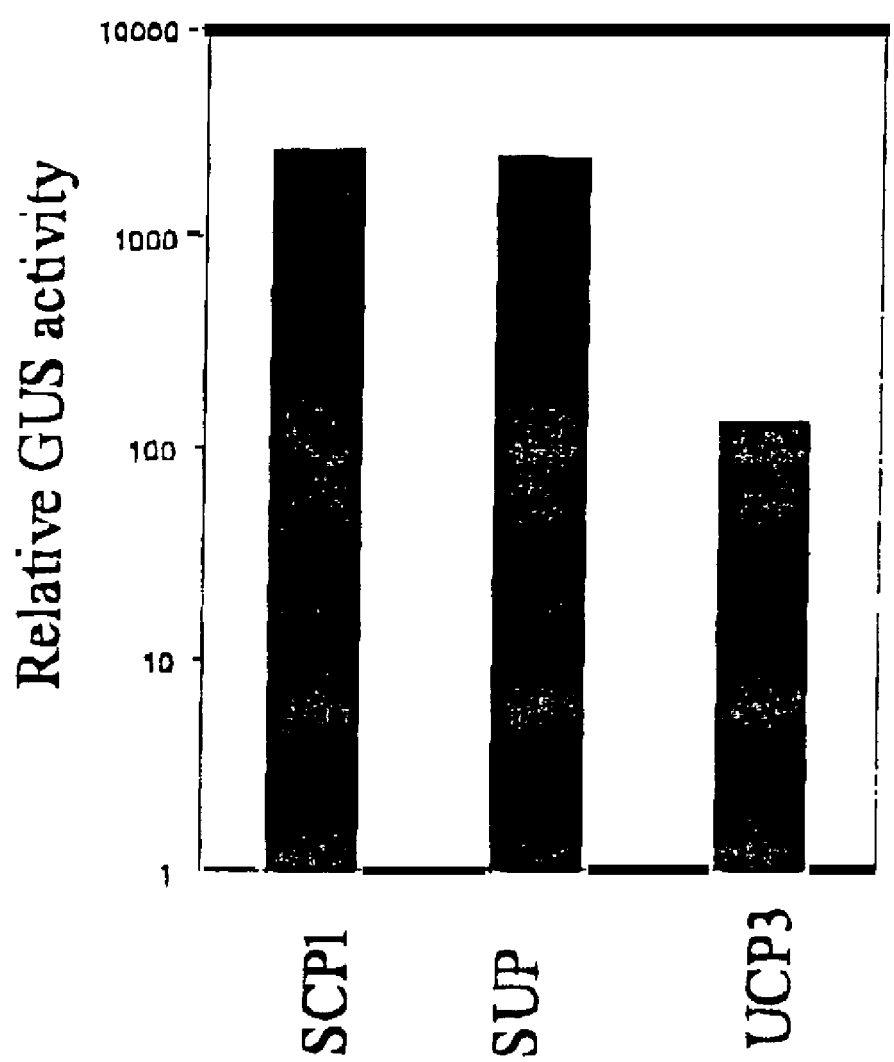
FIG. 2 shows relative β-glucorinidase (GUS) activity of the SCP1, SUP, and UCP3 promoters in uninfected transgenic hairy roots.

UCP3 is not as strong a promoter as the SCP1 promoter in uninfected soybean hairy roots (see FIG. 2). In order to develop a strong and syncytium-active promoter, the 35SUAR-Rsyn7 (enhancer of CaMV 35S promoter plus Rsyn7 element) was cloned with the UbiUAR-Rsyn7-Syn II-core to form the SUP promoter (SEQ ID NO:3). The resulting construct is diagrammatically shown in FIG. 1.

Figure 3:
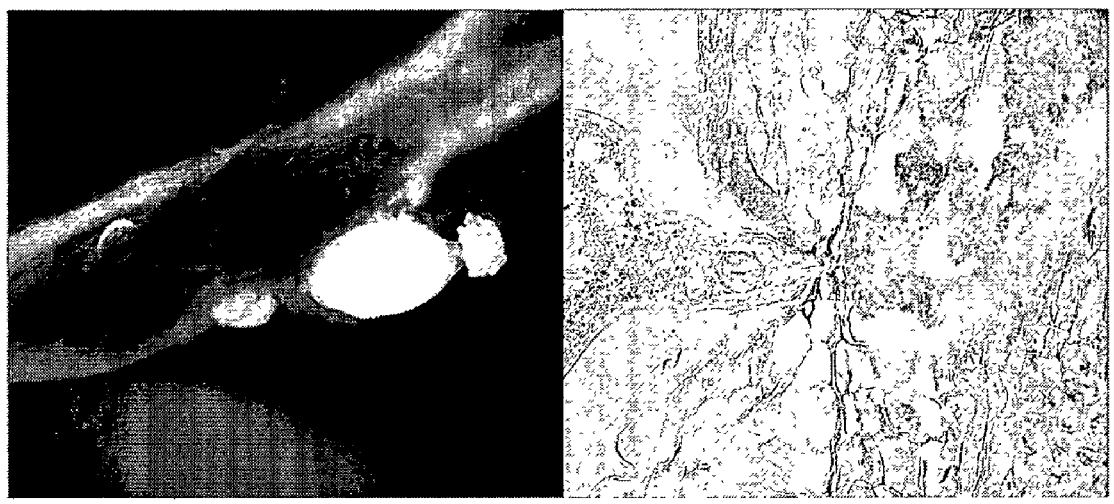
FIG. 3 shows a histochemical analysis of GUS expression in SCN feeding sites. Transgenic hairy roots containing a construct with a SUP promoter were inoculated with SCN strain SCNJ2 and incubated on B5 medium for four weeks. Strong GUS expression was shown both outside and inside syncytium of the infected roots.

On average, uninfected transgenic hairy roots comprising the SUP::GUS construct exhibited stronger SUP-driven GUS activity in comparison to UCP3-driven GUS activity in uninfected transgenic hairy roots comprising the UCP3::GUS construct (FIG. 2). When transgenic hairy roots comprising the SUP::GUS construct were inoculated with soybean cyst nematode (SCN) strain SCNJ2, there was strong SUP-driven GUS activity just outside of and within the feeding site (syncytiun) in the nematode-infected hairy roots (FIG. 3), indicating that SUP promoter activity is also nematode-inducible.

EXAMPLE 8

Soybean Embryo Transformation

Soybean embryos are bombarded with a plasmid containing a heterologous nematode-resistance sequence operably linked to the UCP3 (SEQ ID NO:2) promoter as follows. To induce somatic embryos, cotyledons, 3–5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein et al. (1987) *Nature* (London) 327:70–73, U.S. Pat. No. 4,945,050). A DuPont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell et al. (1985) *Nature* 313:810–812), the hygromycin phosphotransferase gene from plasmid pJR225 (from *E. coli*; Gritz et al. (1983) *Gene* 25:179–188), and the 3' region of the nopaline synthase gene from the T-DNA of the Ti plasmid of *Agrobacterium tumefaciens*. The expression cassette comprising the heterologous nematode-resistance sequence operably linked to the UCP3 promoter can be isolated as a restriction fragment. This fragment can then be inserted into a unique restriction site of the vector carrying the marker gene.

To 50 μl of a 60 mg/ml 1 μm gold particle suspension is added (in order): 5 μl DNA (1 μg/μl), 20 μl spermidine (0.1 M), and 50 μl CaCl$_2$ (2.5 M). The particle preparation is then agitated for three minutes, spun in a microfuge for 10 seconds and the supernatant removed. The DNA-coated particles are then washed once in 400 μl 70% ethanol and resuspended in 40 μl of anhydrous ethanol. The DNA/particle suspension can be sonicated three times for one second each. Five microliters of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

All publications, patents, and patent applications mentioned in the specification are indicative of the level of those skilled in the art to which this invention pertains. All publications, patents, and patent applications are herein incorporated by reference to the same extent as if each individual publication or patent application was specifically and individually indicated to be incorporated by reference in its entirety.

Although the foregoing invention has been described in some detail by way of illustration and example for purposes of clarity of understanding, it will be obvious that certain changes and modifications may be practiced within the scope of the appended claims.

What is claimed is:

1. An isolated nucleic acid molecule comprising a heterologous nematode-resistance sequence operably linked to a promoter which drives expression of said heterologous nematode-resistance sequence in a plant cell, wherein said promoter comprises SEQ ID NO: 3.

2. An expression cassette comprising the nucleic acid molecule of claim 1.

3. A plant cell having stably transformed with the nucleic acid molecule of claim 1.

4. The plant cell of claim 3, wherein said plant cell is from a dicot plant.

5. The plant cell of claim 4, wherein said dicot plant is soybean.

6. An isolated nucleic acid molecule comprising a heterologous nucleotide sequence operably linked to a promoter which regulates expression of said heterologous nucleotide sequence in a plant cell in response to a nematode stimulus, wherein said promoter comprises SEQ ID NO: 3.

7. An expression cassette comprising the nucleic acid molecule of claim 6.

8. A plant cell having stably transformed with the nucleic acid molecule of claim 6.

9. The plant cell of claim 8, wherein said plant cell is from a dicot plant.

10. The plant cell of claim 9, wherein said dicot plant is soybean.

11. An isolated nucleic acid molecule comprising a first nucleotide sequence comprising a heterologous nematode-resistance sequence operably linked to a first promoter which induces expression of said heterologous nematode-resistance sequence in a plant cell and a second nucleotide sequence comprising a nematode resistance inhibitor sequence operably linked to a second promoter which represses transcription of said inhibitor in a plant cell, wherein said first promoter comprises SEQ ID NO: 2 or SEQ ID NO: 3; and said second promoter comprises SEQ ID NO: 1.

12. An expression cassette comprising the nucleic acid molecule of claim 11.

13. A plant cell having stably transformed with the nucleic acid molecule of claim 11.

14. The plant cell of claim 13, wherein said plant cell is from a dicot plant.

15. The plant cell of claim 14, wherein said dicot plant is soybean.

16. A method for expressing a heterologous nematode resistance sequence in a plant, said method comprising transforming a plant cell with a nucleic acid molecule comprising a heterologous nematode-resistance sequence operably linked to a promoter which drives expression of said heterologous nematode-resistance sequence in a plant cell in response to a nematode stimulus, regenerating a stably transformed plant from said plant cell, and exposing said plant to said nematode stimulus, wherein said promoter comprises SEQ ID NO: 3.

17. The method of claim 16, wherein said plant is a dicot.

18. The method of claim 17, wherein said dicot is soybean.

19. The method of claim 16, wherein said heterologous nematode resistance sequence is expressed in root tissues of the plant, wherein said root tissues are selected from the group consisting of pericycle, endodermis and vascular cylinder.

20. A method for expressing a nematode-resistance sequence in a plant, said method comprising transforming a plant cell with a nucleic acid molecule comprising a first nucleotide sequence comprising a heterologous nematode-resistance sequence operably linked to a first promoter which induces expression of said heterologous nematode-resistance sequence in a plant cell and a second nucleotide sequence comprising a nematode resistance inhibitor sequence operably linked to a second promoter which represses transcription of said inhibitor sequence in a plant cell in response to a nematode stimulus, regenerating a stably transformed plant from said plant cell, and exposing said plant to said nematode stimulus, wherein said first promoter comprises SEQ ID NO: 2 or SEQ ID NO: 3; and said second promoter comprises SEQ ID NO: 1.

21. The method of claim 20, wherein said plant is a dicot.

22. The method of claim 1, wherein said dicot is soybean.

23. The method of claim 20, wherein said nematode resistance sequence is expressed in root tissues of the plant, wherein said root tissues are selected from the group consisting of cortex, pericycle, and vascular tissues.

24. A method for altering expression of a heterologous nucleotide sequence in a plant, said method comprising transforming a plant cell with a nucleic acid molecule comprising said heterologous nucleotide sequence operably linked to a promoter which regulates expression of said heterologous nucleotide sequence in a plant cell in response to a nematode stimulus, regenerating a stably transformed plant from said plant cell, and exposing said plant to said nematode stimulus, wherein said promoter comprises SEQ ID NO: 3.

25. The method of claim 24, wherein said plant is a dicot.

26. The method of claim 25, wherein said dicot is soybean.

27. A method for regulating nematode resistance in a plant, said method comprising transforming a plant cell with a nucleic acid molecule comprising a first nucleotide sequence comprising a heterologous nematode-resistance sequence operably linked to a first promoter which induces expression of said heterologous nematode-resistance sequence in a plant cell and a second nucleotide sequence comprising a nematode resistance inhibitor sequence operably linked to a second promoter which represses transcription of said inhibitor sequence in a plant cell in response to a nematode stimulus, regenerating a stably transformed plant from said plant cell, and exposing said plant to said nematode stimulus; wherein said first promoter comprises SEQ ID NO: 2 or SEQ ID NO: 3; and said second promoter comprises SEQ ID NO: 1.

28. The method of claim 27, wherein said plant is a dicot.

29. The method of claim 28, wherein said dicot is soybean.

30. A method of creating or enhancing nematode resistance in a plant, said method comprising transforming a plant cell with a nucleic acid molecule comprising a heterologous nematode-resistance sequence operably linked to a promoter which drives expression of said nematode-resistance sequence in a plant cell in response to a nematode stimulus and regenerating a stably transformed plant from said plant cell, wherein said promoter comprises SEQ ID NO: 3.

31. The method of claim 30, wherein said plant is a dicot.

32. The method of claim 31, wherein said dicot is soybean.

* * * * *

UNITED STATES PATENT AND TRADEMARK OFFICE
CERTIFICATE OF CORRECTION

PATENT NO.        : 7,041,873 B2
APPLICATION NO. : 10/266416
DATED             : May 9, 2006
INVENTOR(S)       : Xu Hu et al.

It is certified that error appears in the above-identified patent and that said Letters Patent is hereby corrected as shown below:

Column 36, Line 55, should read -- represses transcription of said inhibitor sequence in a plant cell, --

Column 37, Line 35, should read --

22. The method of claim 21, wherein said dicot is soybean. --

Signed and Sealed this

First Day of August, 2006

JON W. DUDAS
*Director of the United States Patent and Trademark Office*